(12) United States Patent
Ishikawa et al.

(10) Patent No.: US 11,383,094 B2
(45) Date of Patent: Jul. 12, 2022

(54) CANCER TREATMENT APPARATUS

(71) Applicant: Public University Corporation Yokohama City University, Yokohama (JP)

(72) Inventors: Yoshihiro Ishikawa, Yokohama (JP); Masanari Umemura, Yokohama (JP); Taisuke Akimoto, Yokohama (JP)

(73) Assignee: Public University Corporation Yokohama City University, Yokohama (JP)

( * ) Notice: Subject to any disclaimer, the term of this patent is extended or adjusted under 35 U.S.C. 154(b) by 164 days.

(21) Appl. No.: 16/463,061

(22) PCT Filed: Nov. 22, 2017

(86) PCT No.: PCT/JP2017/042029
§ 371 (c)(1),
(2) Date: Aug. 6, 2019

(87) PCT Pub. No.: WO2018/097185
PCT Pub. Date: May 31, 2018

(65) Prior Publication Data
US 2019/0351250 A1 Nov. 21, 2019

(30) Foreign Application Priority Data
Nov. 24, 2016 (JP) .............................. JP2016-228164

(51) Int. Cl.
*A61N 2/02* (2006.01)
(52) U.S. Cl.
CPC ..................................... *A61N 2/02* (2013.01)

(58) Field of Classification Search
CPC . A61N 2/02; A61N 2/00; A61N 2/004; A61N 2/006; A61N 2/008
See application file for complete search history.

(56) References Cited

U.S. PATENT DOCUMENTS

| 4,665,898 | A | 5/1987 | Costa et al. |
| 6,424,864 | B1 | 7/2002 | Matsuura |
| 2004/0210102 | A1* | 10/2004 | van Mullekom ........ A61N 2/02 600/9 |
| 2005/0090732 | A1 | 4/2005 | Ivkov et al. |
| 2009/0043346 | A1 | 2/2009 | Palti et al. |
| 2016/0143859 | A1 | 5/2016 | Brossel |
| 2016/0256704 | A1* | 9/2016 | Petty ..................... A61N 2/004 |

(Continued)

FOREIGN PATENT DOCUMENTS

| EP | 0361797 A | 4/1990 |
| JP | S63-068180 A | 3/1988 |

(Continued)

OTHER PUBLICATIONS

International Search Report for PCT/JP2017/042029 dated Feb. 27, 2018 and English translation thereof.

(Continued)

*Primary Examiner* — Christine H Matthews
(74) *Attorney, Agent, or Firm* — Muncy, Geissler, Olds & Lowe, P.C.

(57) ABSTRACT

A cancer treatment apparatus including a magnetic field generator that generates a magnetic field of 100 kHz to 300 kHz to be applied to affected tissues.

6 Claims, 29 Drawing Sheets

(56) References Cited

U.S. PATENT DOCUMENTS

2016/0317830 A1* 11/2016 Hirayama ............... A61N 2/02
2017/0189707 A1*  7/2017 Zabara .................... A61N 1/40

FOREIGN PATENT DOCUMENTS

| JP | H01-244767 A  | 9/1989  |
| JP | H02-088059 A  | 3/1990  |
| JP | H03-158176 A  | 7/1991  |
| JP | 2005-230567 A | 9/2005  |
| JP | 2007-521109 A | 8/2007  |
| JP | 4750784 B2    | 8/2011  |
| JP | 5485153 B2    | 5/2014  |
| JP | 2016-532674 A | 10/2016 |
| WO | 2015/070036 A1| 5/2015  |
| WO | 2015/142922 A1| 9/2015  |

OTHER PUBLICATIONS

Jordan, A. et al., Presentation of a new magnetic field therapy system for the treatment of human solid tumors with magnetic fluid hyperthermia, Journal of Magnetism and Magnetic Materials, 2001, vol. 225, issues 1-2, pp. 118-126.
Extended European search report of the corresponding EP application No. 17873062.8 dated Jun. 5, 2020.
Office Action for JP counterpart application No. 2018-552621 dated Jun. 11, 2019 and English machine translation thereof.
Communication pursuant to Article 94(3) EPC for the corresponding EP application No. 17873062.8 dated Jun. 8, 2021.

* cited by examiner

FIG.3

| CANCER TYPE INPUT UNIT | MEMORY | | |
|---|---|---|---|
| DISEASE NAME | CANCER TYPE PARAMETER | FREQU-ENCY (kHZ) | APPLICATION DURATION (MINUTES PER ONE APPLICATION) |
| GLIOBLASTOMA MODE 1 → | HUMAN GLIOBLASTOMA MODE 1 | 196 | 30 |
| GLIOBLASTOMA MODE 2 → | HUMAN GLIOBLASTOMA MODE 2 | 227 | 30 |
| GLIOBLASTOMA MODE 3 → | HUMAN GLIOBLASTOMA MODE 3 | 280 | 30 |
| MALIGNANT MELANOMA MODE 1 → | HUMAN MALIGNANT MELANOMA MODE 1 | 196 | 30 |
| MALIGNANT MELANOMA MODE 2 → | HUMAN MALIGNANT MELANOMA MODE 2 | 227 | 30 |
| MALIGNANT MELANOMA MODE 3 → | HUMAN MALIGNANT MELANOMA MODE 3 | 280 | 30 |
| TONGUE CANCER MODE 1 → | HUMAN TONGUE CANCER MODE 1 | 196 | 30 |
| TONGUE CANCER MODE 2 → | HUMAN TONGUE CANCER MODE 2 | 227 | 30 |
| BREAST CANCER MODE 1 → | HUMAN BREAST CANCER MODE 1 | 196 | 30 |
| BREAST CANCER MODE 2 → | HUMAN BREAST CANCER MODE 2 | 227 | 30 |
| BREAST CANCER MODE 3 → | HUMAN BREAST CANCER MODE 3 | 280 | 30 |

FIG.4
(a)
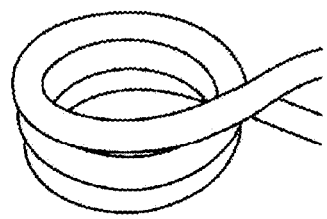
(b)
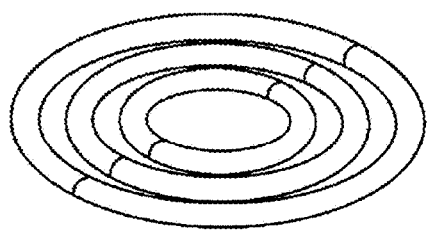
(c)
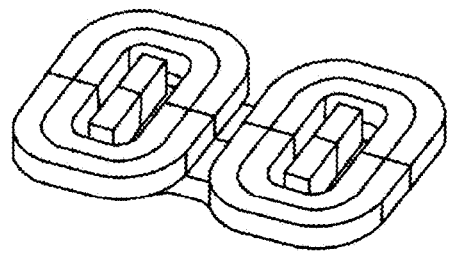

FIG.12
(a) 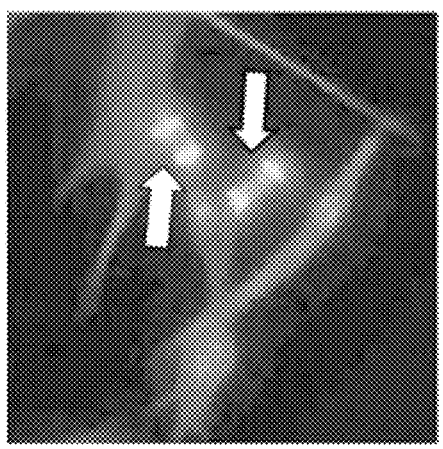  (b) 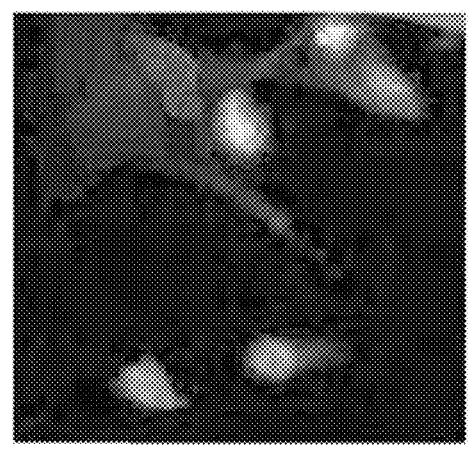

FIG. 16
(a)
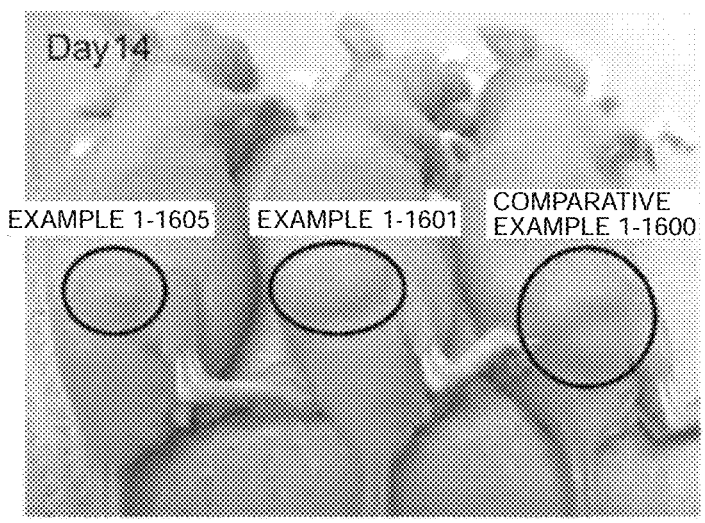
(b)
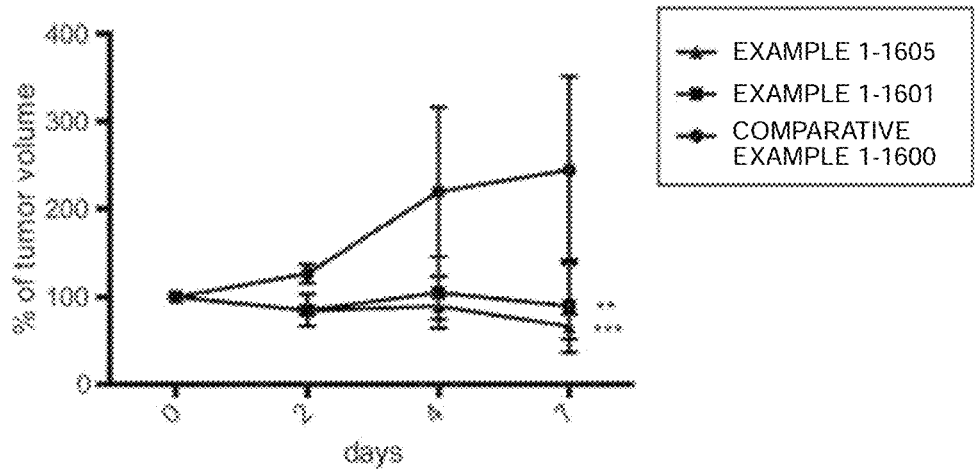
(c)
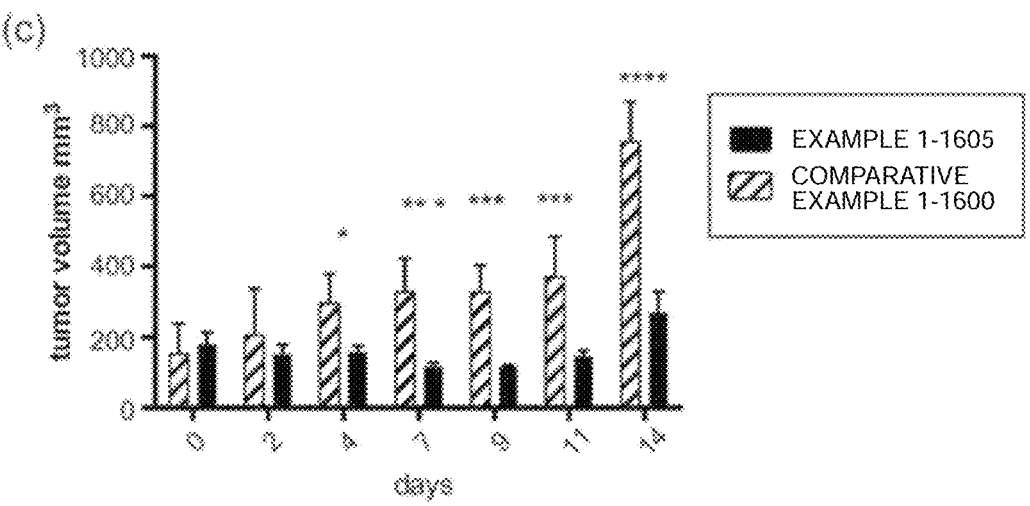

FIG.17

| CANCER TYPE INPUT UNIT | | MEMORY | | | |
|---|---|---|---|---|---|
| DISEASE NAME | | CANCER TYPE PARAMETER | FREQUENCY (KHZ) | APPLICATION DURATION (MINUTES PER ONE APPLICATION) | THE NUMBER OF TIMES OF APPLICATIONS (DAYS/WEEK) |
| GLIOBLASTOMA MODE 1 | → | HUMAN GLIOBLASTOMA MODE 1 | 227 | 30 | 1 |
| GLIOBLASTOMA MODE 2 | → | HUMAN GLIOBLASTOMA MODE 2 | 227 | 30 | 5 |

FIG. 18
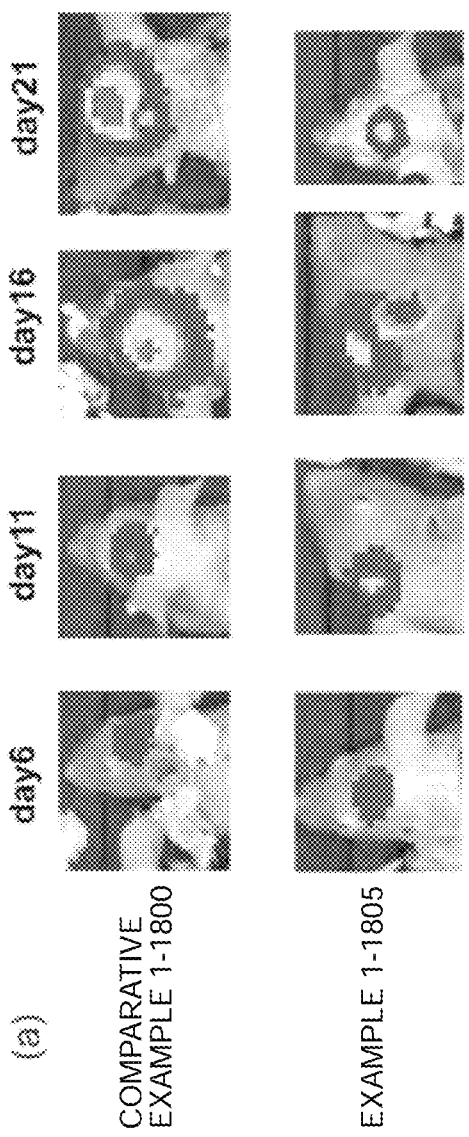
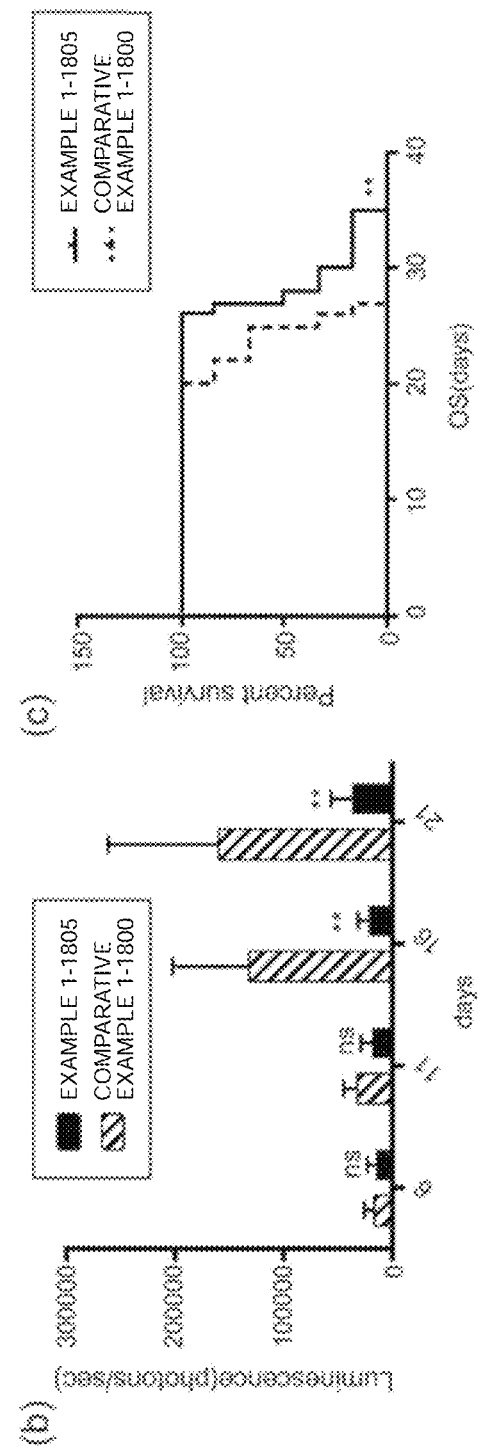

FIG. 24

| | 15 DAYS UNDER SKIN | | 90 DAYS INSIDE CRANIUM |
|---|---|---|---|
| | ONCE-A-WEEK GROUP | 5-TIMES-A-WEEK GROUP | 5-TIMES-A-WEEK GROUP |
| CLINICAL SIGN | NONE | NONE | NONE |
| SKIN DISORDER | NONE | NONE | NONE |
| REDUCTION OF BODY WEIGHT | NONE | NONE | NONE |
| REDUCTION OF FOOD INTAKE | NONE | NONE | NONE |
| DEGRADATION OF BIOLOGICAL FUNCTION | NONE | NONE | NONE |
| DEGRADATION OF KIDNEY FUNCTION | NONE | NONE | NONE |
| REDUCTION OF PANHEMOCYTES | — | — | NONE |

# CANCER TREATMENT APPARATUS

TECHNICAL FIELD

The present invention relates to a cancer treatment apparatus for suppressing proliferation of cancer cells by applying an alternating magnetic field to affected tissues.

BACKGROUND ART

Conventionally, there have been proposed apparatuses for applying an electric field to the affected tissues as cancer treatment apparatuses for highly malignant cancers. PTL 1 discloses an apparatus which selectively destroys or inhibits the growth of rapidly dividing cells located within a target region of a patient and which includes: an AC voltage source; and a plurality of insulated electrodes that are operatively connected to the AC voltage source, wherein each of the electrodes has a surface configured for placing against the patient's body; wherein the AC voltage source and the electrodes are configured so that, when the electrodes are placed against the patient's body, a first AC electric field having a first frequency and a second AC field having a second frequency are imposed sequentially in terms of time in the target region of the patient, wherein the first frequency and the second frequency are different, wherein the first and second electric fields have frequency characteristics that correspond to a vulnerability of the rapidly dividing cells, wherein the first and second electric fields are strong enough to damage, during the late anaphase or telophase stages of cell division, a significant portion of the rapidly dividing cells whose long axis is generally aligned with the lines of force of the electric fields, and wherein the first and second electric fields leave non-dividing cells located within the target region substantially unchanged.

Moreover, PTL 2 proposes an in-vitro method of selectively destroying or inhibiting the growth of parasites located within a target region (1620), including the steps of: capacitively coupling an AC electric field into the target region (1620); and repeating the coupling step until a therapeutically significant portion of the parasites die within the target region (1620), wherein the frequency of the electric field is between 10 MHz and 20 MHz, wherein the strength of the electric field in at least a portion of the target region (1620) is between 0.5 V/cm and 10 V/cm, wherein the electric field damages or disrupts a significant portion of the parasites positioned within the target region (1620), and wherein the electric field leaves non-dividing cells located within the target region (1620) substantially unharmed.

However, with the cancer treatment apparatus which applies the electric field to the affected part, it is necessary to shave the affected part in order to mount electrode section of the apparatus. Additionally, duration to wear the electrode sections is long and it is sometimes necessary to wear the electrode sections for 18 hours or longer. Furthermore, if a patient moves during the time when they wear the apparatus, they are forced to carry a heavy power source. In light of the current use situation of the cancer treatment apparatus, there is a demand for a cancer treatment apparatus which not only has the therapeutic effects, but also is suited for a remission treatment with less burden on patients.

There is another cancer treatment apparatus proposed by PTL 3, that is, a ceramic heating element for a thermotherapy characterized in that the ceramic heating element is ferromagnetic ferrite particles covered with a bioactive inorganic layer and has a very good affinity for surrounding tissues when embedded in a body and generates heat via magnetic induction highly efficiently within an alternating magnetic field. Furthermore, PTL 4 discloses a cancer treatment apparatus characterized in that it includes: a pair of magnetic poles for generating an alternating magnetic field, wherein the magnetic poles are set at positions opposite each other to sandwich an affected part in a manner such that a clearance between them can be freely adjusted; a magnetic field application unit for applying the alternating magnetic field to the pair of magnetic poles; and a magnetic field control module for controlling the alternating magnetic field.

The inventions described in PTL 3 and PTL 4 are embedded in the body for a long period of time and thereby intended for the cancer treatment by means of their hyperthermia effects. However, specific cancer cell cytostatic effects are not disclosed. Therefore, it is desired that the cancer treatment by application of the magnetic field be further studied and a cancer treatment apparatus which exhibits revolutionary effects on highly malignant cancer cells be established based on achievements of such study.

CITATION LIST

Patent Literature

PTL 1: Japanese Patent No. 4750784
PTL 2: Japanese Patent No. 5485153
PTL 3: Japanese Patent Application Laid-Open Publication No. H02-88059
PTL 4: Japanese Patent Application Laid-Open Publication No. H03-158176

SUMMARY OF THE INVENTION

Problems to be Solved by the Invention

It is an object of the present invention to provide a low-cost cancer treatment apparatus suited for a remission treatment.

Means to Solve the Problems

A cancer treatment apparatus according to a first embodiment of the present invention includes a magnetic field generator that generates a magnetic field of 100 kHz to 300 kHz to be applied to affected tissues. The present invention is the cancer treatment apparatus which applies the magnetic field of 100 kHz to 300 kHz by placing the magnetic field generator opposite the affected tissues. The present invention can suppress the proliferation of cancer cells by applying the magnetic field from the magnetic field generator to the affected tissues. The magnetic field generator according to the present invention can apply the magnetic field, which is required to obtain a specified operational advantage of the present invention, to an affected part even in a state not in contact with the affected part. Accordingly, the present invention should preferably be used by placing the magnetic field generator opposite the affected tissues in a non-contact state. Incidentally, the temperature of the magnetic field generator upon the generation of the magnetic field is approximately from 30° C. to 39° C., inclusive, so that even if the magnetic field generator contacts the affected tissues, the affected tissues can be treated safely. Therefore, the present invention can be also used in the state where the affected tissues and the magnetic field generator are placed opposite each other and in contact with each other.

The present invention contains the cancer treatment apparatus stated in claim 1, which further includes: a control module that controls an electric current supplied to the magnetic field generator; and a power source that supplies an alternating current to the magnetic field generator on the basis of output from the control module, wherein the control module includes: a cancer type input unit that accepts input of a cancer type of the affected tissues; a storage unit that stores a frequency corresponding to the cancer type; and a controller that refers to the storage unit and sets the frequency corresponding to the cancer type, which is input to the cancer type input unit, to the power source.

The present invention contains the cancer treatment apparatus which further stores application duration corresponding to the cancer type; and the controller refers to the storage unit and outputs information of the application duration corresponding to the cancer type, which is input to the cancer type input unit, to the power source. Accordingly, the present invention can simplify the input of the application duration by an operator and contribute to the reduction of a patient's burden. The present invention contains the cancer treatment apparatus which includes a power switch that starts supplying the alternating current from the power source to the magnetic field generator. The present invention contains the cancer treatment apparatus which controls a temperature of the affected tissues to make it lower than a cancer cell killing temperature. Accordingly, the proliferation of the cancer cells can be suppressed at a temperature lower than the cancer cell killing temperature. The present invention contains the cancer treatment apparatus regarding which the affected tissues are human affected tissues.

The present invention contains the cancer treatment apparatus which includes a cancer type input unit capable of selecting and inputting one cancer type from a group consisting of a glioblastoma, a malignant melanoma, a tongue cancer, a breast cancer, a malignant mesothelioma, a pancreatic cancer, and a human alveolar basal epithelial adenocarcinoma. Regarding cancer treatments, preferred alternating magnetic field conditions to obtain therapeutic effects vary depending on the cancer type. The present invention can intuitively input the frequency and application duration which are suited for the treatment target cancer type and contribute to the reduction of the operator's burden.

According to the present invention, the application duration should preferably be configured as a value within a range of 30 minutes to 180 minutes, inclusive.

Advantageous Effects of the Invention

The present invention can apply a specific alternating magnetic field, which is suited for suppressing the proliferation of the cancer cells, to the affected tissues. Regarding the present invention, the magnetic field generator which applies the magnetic field to the affected tissues can be a non-contact type. The application duration is short and additionally the apparatus is lightweight. Therefore, the present invention is suited for the remission treatment.

BRIEF DESCRIPTION OF DRAWINGS

FIG. 3 is an example of a cancer type input unit according to the present invention;
FIG. 4 illustrates shape examples of a coil(s) used for a magnetic field generator according to the present invention;
FIG. 12 shows observation results of cancer cells to which the example of the present invention is applied;
FIG. 16 shows observation results of changes in the tumor volume according to the example of the present invention;
FIG. 17 is an example of the cancer type input unit according to the present invention;
FIG. 18 shows observation results of tumor models according to the working example of the present invention;
FIG. 24 shows observation results of side effects according to the example of the present invention.

DESCRIPTION OF EMBODIMENTS

Figure 1:
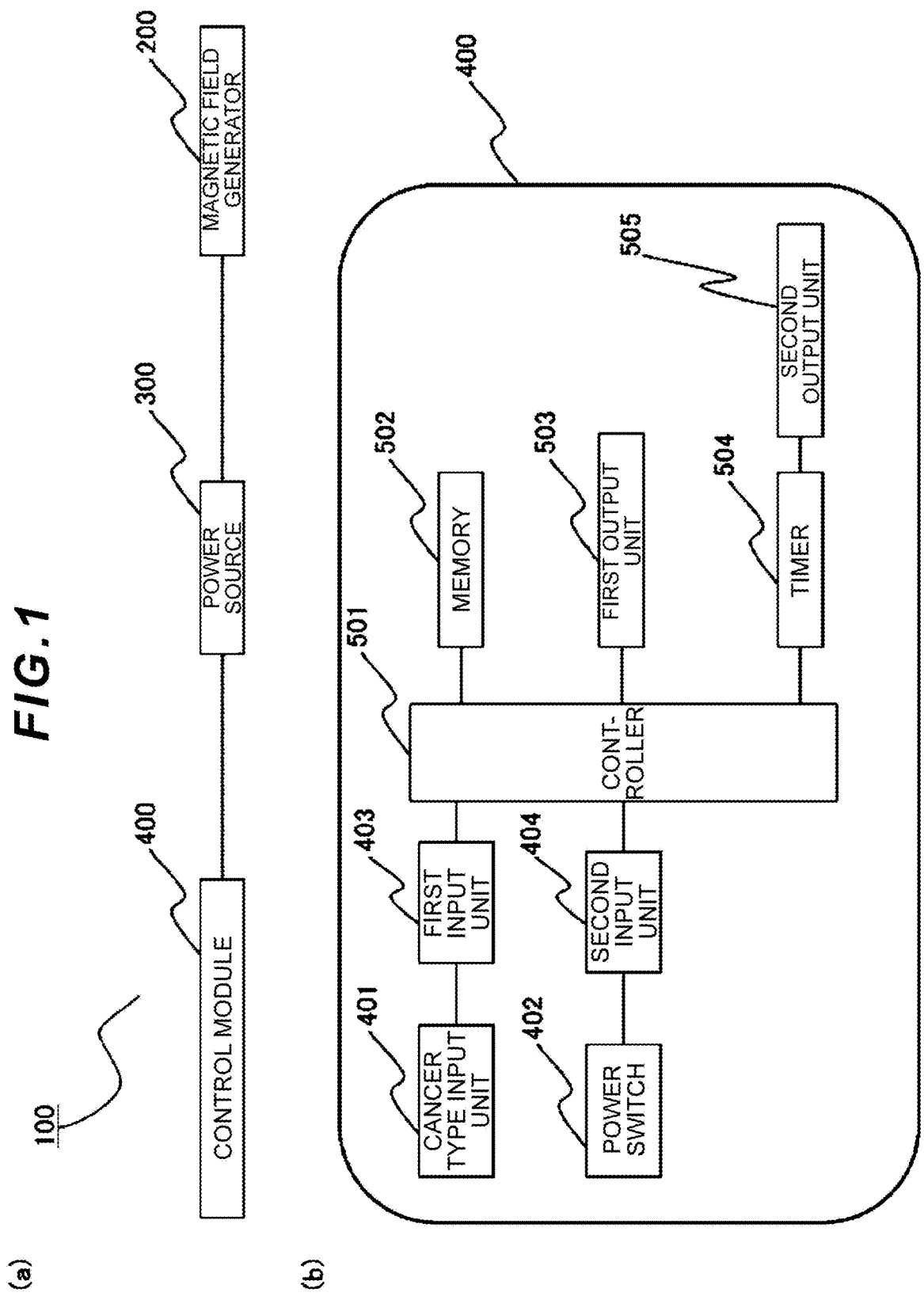
FIG. 1 is a conceptual diagram of an example of a cancer treatment apparatus according to the present invention.
Figure 2:
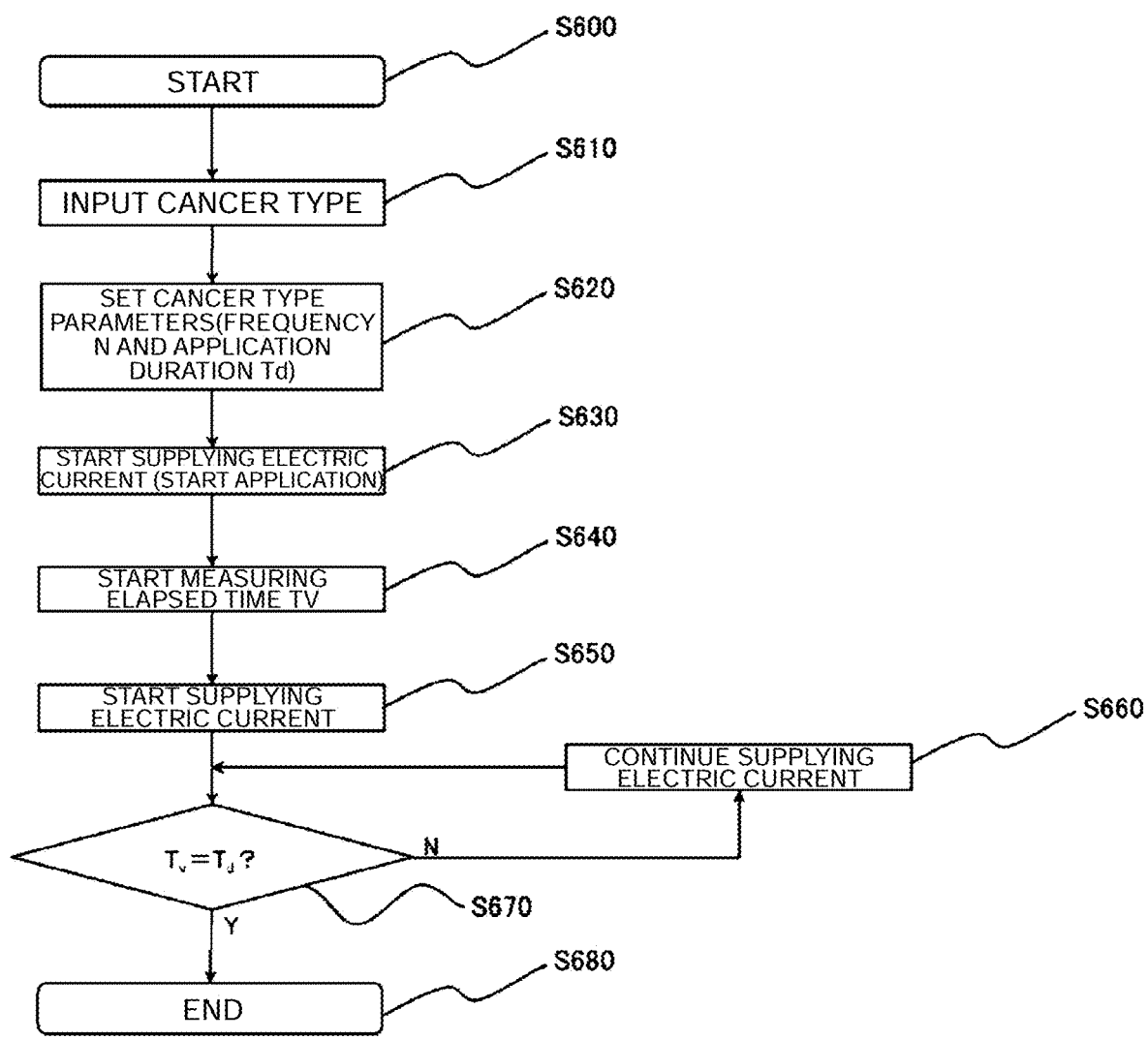
FIG. 2 is an example of a flowchart of the cancer treatment apparatus according to the present invention.

An embodiment of the present invention will be explained with reference to FIG. 1 and FIG. 2. FIG. 1 is a conceptual diagram of an example of a cancer treatment apparatus according to the present invention. FIG. 2 is a flowchart of the cancer treatment apparatus according to the present invention. Referring to FIG. 1(a), 100 represents a cancer treatment apparatus, 200 represents a magnetic field generator, 300 represents a power source, and 400 represents a control module. The magnetic field generator 200 includes a cooling mechanism, such as cooling fans, which is not illustrated in the drawing and maintains an appropriate temperature of the magnetic field generator 200.

FIG. 1(b) is a conceptual diagram for explaining the control module 400 illustrated in FIG. 1(a). 401 represents a cancer type input unit, 402 represents a power switch, 403 represents a first input unit, 404 represents a second input unit, 501 represents a controller, 502 represents a memory, 503 represents a first output unit, 504 represents a timer, and 505 represents a second output unit. The control module 400 includes a CPU that is a central processing unit which is not illustrated in the drawing, a ROM which is a read-only storage area, and a RAM which is readable and writable; and the CPU implements the operation described later by expanding programs stored in the ROM onto the RAM and executing them. However, the control module 400 may implement the operation described later via a hardware circuit.

FIG. 2 explains an example of applying a magnetic field by setting a cancer type parameter which is a combination of a frequency parameter and an application duration parameter. The frequency parameter and the application duration parameter which are stored in the memory 502 can be evoked and desired frequency and application duration can be set by activating the present invention, selecting a disease name and a cancer type, and inputting them to the cancer type input unit 401. FIG. 3 illustrates an example of the cancer type input unit. Referring to FIG. 3, a disease name column corresponds to the cancer type input unit 401. The cancer type input unit 401 should preferably display the disease name from the viewpoint of convenience for the operator; however, the invention is not limited to this example and, for example, a cancer type may be displayed.

Regarding numerical values indicated in columns of the frequency and the application duration in FIG. 3, preferred values corresponding to the disease name and the cancer type are associated with such numeral values, so that they do not have to be displayed in the cancer type input unit. However, the present invention does not exclude an embodiment to display these values in visually recognizable positions. Incidentally, a preferred mechanism for inputting data to the cancer type input unit should include devices such as a keyboard and a mouse, a touch panel, and so on.

Furthermore, when it is designed so that a plurality of application modes can be set for the same disease name, it is also preferable that a mode name be assigned to the disease name as illustrated in FIG. 3. The following explanation will be provided by taking an embodiment to set "Glioblastoma Mode 2" as an example.

When "Glioblastoma Mode 2" is input to the cancer type input unit 401 (S610), the cancer type parameter which is a combination of the frequency of 227 kHz and the application duration of 30 minutes per one application is evoked from the memory 502 via the first input unit 403 and the frequency N and the application duration $T_d$ are set respectively upon application of the magnetic field (S620). After placing the affected part opposite the magnetic field generator 200 and switching the power switch 402 to ON, the power source 300 is notified of supply of an alternating current at the frequency of 227 kHz via the first output unit 503 and the second input unit 404 from the power source 300 to the magnetic field generator 200 and the supply of the electric current is started (S630). Consequently, the magnetic field generator 200 starts applying the alternating magnetic field to the affected tissues. Incidentally, at the same time as the start of the electric current supply, the timer 504 starts measuring elapsed time $T_v$ from the start of the electric current supply (S640). The electric current continues to be supplied until the elapsed time $T_v$ becomes equal to the application duration $T_d$ (30 minutes in this embodiment), that is, while $T_v \neq T_d$ (S660). After the elapse of 30 minutes from the start of the electric current supply, that is, when the elapsed time $T_v$ becomes equal to the application duration $T_d$ ($T_v = T_d$) (S670), the power source 300 is notified of the completion of the application duration via the second output unit 505, the electric current supply to the magnetic field generator 200 is stopped, and the application of the magnetic field to the affected part is terminated (S680). Regarding stoppage of the electric current supply, a mechanism for forcibly stopping the supply may be provided within the apparatus, or a notification means such as an alarm may be provided and the supply may be stopped manually.

The frequency parameter which is stored in the memory according to the present invention should preferably be a value within the range of 100 kHz to 300 kHz, inclusive. When the frequency parameter is less than 100 kHz, any significant cancer cell cytostatic effect will not be obtained even if the magnetic field is applied. When the frequency parameter exceeds 300 kHz, there is a possibility that the effect might attenuate. Also, as compared to the case where the frequency parameter is equal to or less than 300 kHz, there is a possibility that the temperature of the magnetic field generator might increase. The frequency at which the cancer cell cytostatic effect may tend to appear easily varies depending on the cancer type of a magnetic field application target. Regarding values stored in the memory as the frequency parameter for a glioblastoma, a malignant melanoma, a tongue cancer, a breast cancer, and a malignant mesothelioma, it is possible to store values which are dispersed at regular intervals, for example, every 50 kHz, that is, 100 kHz, 150 kHz, 200 kHz, 250 kHz, and 300 kHz. Alternatively, specific values such as 196 kHz, 227 kHz, 280 kHz, and 389 kHz may be stored or the respective parameters may be dispersed at irregular intervals and stored with reference to a specified frequency for each cancer type. For example, it is an embodiment where a relatively small interval(s) is set around a most preferred value and a relatively large interval(s) is set around a maximum value and a minimum value.

The application duration parameter stored in the memory according to the present invention should preferably be a value within the range of 30 minutes to 180 minutes, inclusive. When the application duration is less than 30 minutes, any significant cancer cell cytostatic effect will not be obtained even if the magnetic field is applied. If the present invention is used for 30 minutes or longer, the significant cancer cell cytostatic effect will be obtained even if the application duration is equal to or less than 180 minutes. Therefore, when using the present invention, it is unnecessary to apply the magnetic field to the affected part for a long period of time and the patient's burden can be thereby reduced. Additionally, since operating time of the present invention per patient is short, a plurality of patients can take turns using one apparatus of the present invention in one day. Furthermore, since the present invention can be used in the state of placing the affected tissues not in contact with the magnetic field generator, hygienic maintenance required when the user is switched is easy. As a result, the present invention contributes to cost reduction.

The application duration which brings about the cancer cell cytostatic effect in a preferable manner varies depending on the cancer type and the frequency. When the application duration is stored in the memory as the application duration parameter for the glioblastoma, malignant melanoma, tongue cancer, breast cancer, and malignant mesothelioma, it is possible to store, as an example, 30 minutes, 45 minutes, 60 minutes, 120 minutes, and 180 minutes. The frequency and the application duration may be set individually. In that case, a first cancer type input unit for setting the frequency and a second cancer type input unit for setting the application duration may be provided. In that case, as a result of input to the first and second cancer type input units, the frequency parameter and the application duration parameter are evoked individually from the memory and the specified frequency and application duration are set respectively. From the viewpoint of convenience of the present invention, it is preferable as explained with reference to FIG. 3 that a combination of the frequency and the application duration be set as the cancer type parameter.

Furthermore, it is also preferable that according to the present invention, the number of times of applications be set according to the size of the relevant tumor, its progression, and the condition of the patient such as their physical condition. Therefore, it is also preferable that the present invention be configured to be capable of storing a parameter of the number of times of applications in the memory and setting the number of times of applications by making an input to the cancer type input unit. Furthermore, if the cancer type parameter is combined with the parameter of the number of times of applications, the frequency parameter, and the application duration parameter, not only the frequency and the application duration, but also the number of times of applications can be set by one input. Accordingly, the present invention can prevent errors in a magnetic field application schedule and further reduce the user's burden of operation.

The number of times of applications according to the present invention should preferably be once a day or may be one day per week or also preferably be consecutive five days or more per week. For example, when the number of times of applications is set as consecutive five days, the magnetic field can be applied according to the present invention by setting the application start day as the 1st day, applying the magnetic field once every day from the 1st day to the 5th day, and not applying the magnetic field on the 6th day and the 7th day. Since the application duration per one application according to the present invention is short, it hardly becomes the user's burden even if the number of times of applications increases. Furthermore, the definition of the number of times of applications is not limited to the number of times per week. Specifically speaking, the number of times of applications may be set for a cycle such as per five days or per two weeks.

It is preferable that a coil be used as the magnetic field generator according to the present invention. Examples of the shape of the coil can include a helical type and a disc type. FIG. 4 illustrates examples of the coil shape used for the magnetic field generator according to the present invention. Referring to FIG. 4, FIG. 4(a) is a helical-type coil obtained by molding a metal wire in a helical shape; FIG. 4(b) is a disc-type coil obtained by molding the metal wire in a spiral shape; FIG. 4(c) is a double-disc-type coil formed by placing two disc-type coils illustrated in FIG. 4(b) side by side. When the coil of any one of the shapes is used, the present invention can suppress the proliferation of the cancer cells by applying the magnetic field without placing the magnetic field generator and the affected tissues in contact with each other.

Figure 5:
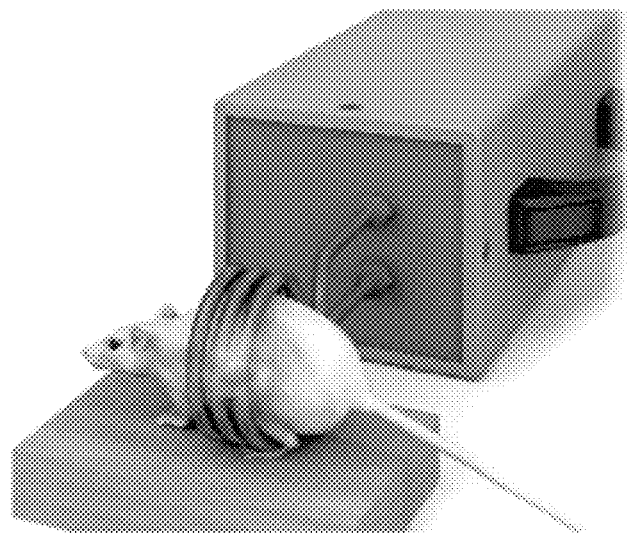
FIG. 5 is an application example of the present invention.

The magnetic field generator according to the present invention may be configured so that the coil of a single shape is secured; however, it is preferable that coils of a plurality of shapes be made replaceable. Accordingly, the magnetic field generator can be formed by selecting and attaching the coil of a preferred shape to the site of the affected part, depending on whether the affected part is located at any one of a head, four limbs, a torso, and other sites. As a result, the magnetic field can be applied more efficiently to the affected part. The present invention can be used as it is placed opposite the affected tissues and without contacting the affected tissues. Additionally, as the magnetic field generator includes a replaceable coil, its versatility can be further enhanced. Also, the coil to be secured to the magnetic field generator may be a combination of a plurality of coils with different properties. FIG. 5 illustrates an application example of the present invention. FIG. 5 illustrates an embodiment in which the magnetic field generator including the helical-type coil is placed opposite an individual (mouse) having an affected part in its torso and the alternating magnetic field is applied to the individual.

Figure 27:
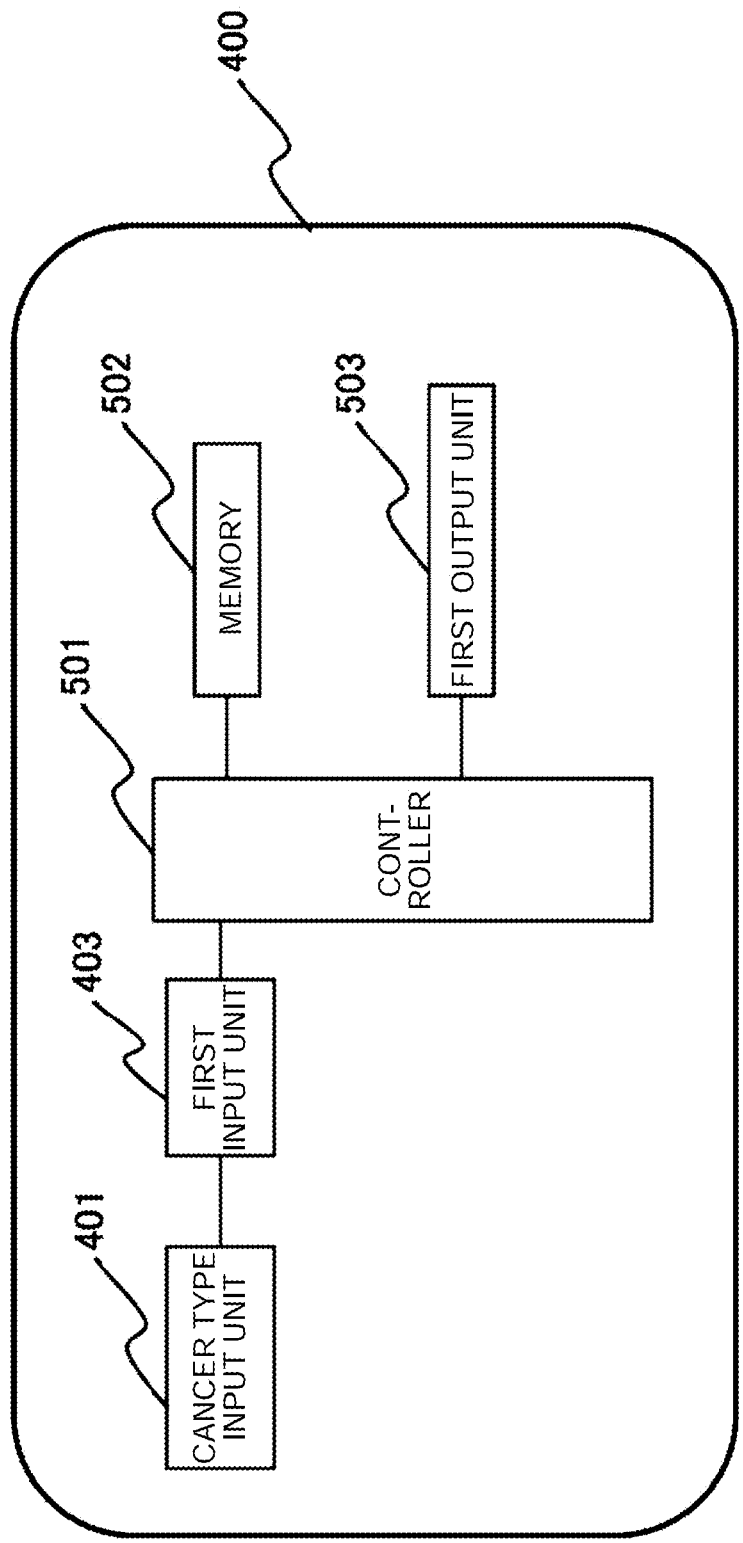
FIG. 27 is a conceptual diagram of another example of the cancer treatment apparatus according to the present invention.

Incidentally, the control module 400 may not include the power switch 402 or the timer 504. In this case, the configuration of the control module 400 is as illustrated in FIG. 27 and the control module 400 may not include the second input unit 404 or the second output unit 505. In this case, the control module 400 can implement the same operation as the case where the power switch 402 and the timer 504 are included, by controlling the electric power supplied to the power source 300 from outside the cancer treatment apparatus 100. Furthermore, the control module 400 may not include either one of the power switch 402 and the timer 504. However, when the control module 400 includes the power switch 402, the second input unit 404 is also included; and when the control module 400 includes the second input unit 404, the second output unit 505 is also included.

Figure 28:
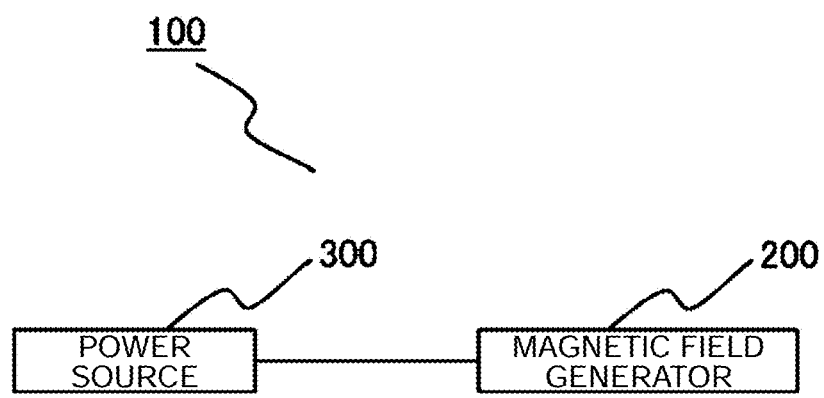
FIG. 28 is a conceptual diagram of further another example of the cancer treatment apparatus according to the present invention.

Furthermore, the cancer treatment apparatus 100 may be configured so that the control module 400 is not included and the magnetic field generator 200 generates the magnetic field at a fixed frequency of any value from 100 kHz to 300 kHz. The configuration of the cancer treatment apparatus 100 in this case is as illustrated in FIG. 28. Furthermore, the frequency of the magnetic field generated by the magnetic field generator 200 may be from 200 kHz to 300 kHz.

Furthermore, the control module 400 may control the temperature of the affected tissues to become lower than a cancer cell killing temperature. Specifically speaking, a temperature range of 40° C. to 43° C. is known as the cancer cells killing temperature, so that the control module 400 may control the temperature of the affected tissues to become lower than 40° C. In this case, the control module 400 specifies conditions to apply the magnetic field and duration when the magnetic field may be continuously radiated for each cancer type, by referring to a database prepared in advance; and radiation duration, that is, the duration set to the timer 504 is set to be less than the duration obtained from the database.

EXAMPLES

The present invention will be explained by using an example in which a copper-made, helical-type coil (inner diameter of a helical part: 4 cm; outer diameter of the helical part: 5 cm; the number of elements 430,998/the number of nodes 137,055; and conductivity: 1.673e-8 [ohm m]) is used as the magnetic field generator. Unless particularly explained, the electric current supplied to the magnetic field generator is 250 A. This example is Example 1. However, the present invention is not limited to Example 1 as long as it exerts its operational advantages.

1. Magnetic Flux Density of Example 1

Figure 6:
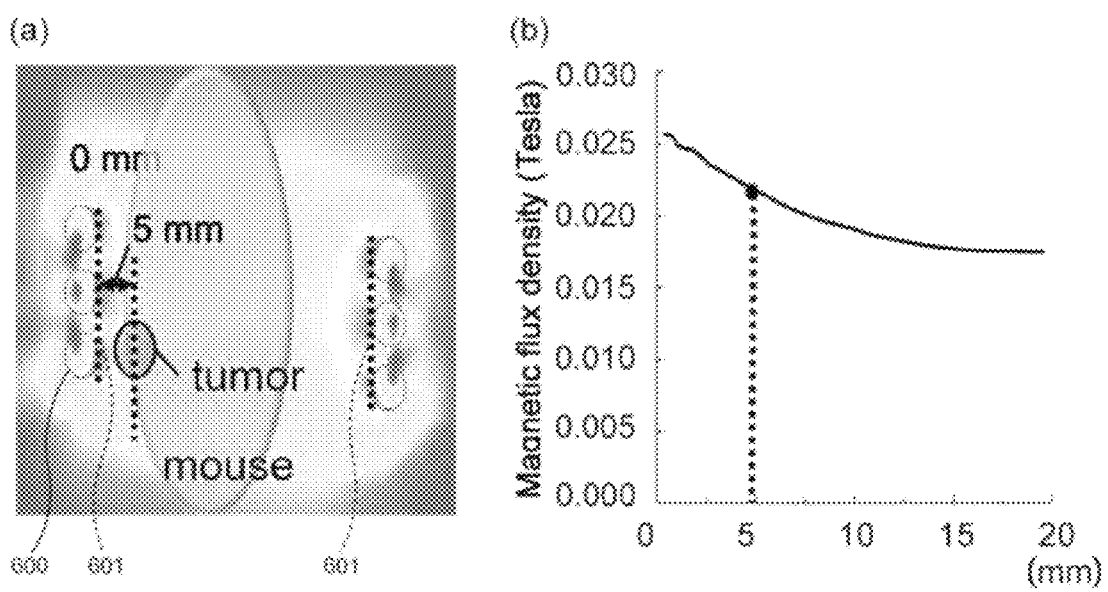
FIG. 6 is a simulation result of magnetic flux density regarding a magnetic field generator according to a example of the present invention.

FIG. 6 is a simulation result of magnetic flux density of the magnetic field generator of Example 1. FIG. 6(b) shows the magnetic flux density when the torso of the individual (mouse) was placed opposite a helical-part inner diameter face 601 of a coil 600 of the magnetic field generator in a state illustrated in FIG. 6(a) and an electric current of 335.4 A with the frequency of 280 kHz was applied. The distance indicated by x-axis in FIG. 6(b) is a vertical distance from the helical-part inner diameter face 601 of the coil 600 illustrated in FIG. 6(a), that is, a 0-mm surface to the helical shaft center side. Five (5) mm along x-axis in FIG. 6(b) means an area 5 mm away from the 0-mm surface towards the helical shaft center side (inside) as illustrated in FIG. 6(a). As a result of simulation of the magnetic flux density under measurement conditions for the magnetic flux density as described below, it was found that the increase of the distance as illustrated in FIG. 6(b) caused a mild influence on the reduction of the magnetic flux density and the magnetic flux density of the relevant area was 21 mT. When the magnetic field generator according to the present invention is placed opposite the affected tissues in a non-contact state, the distance between the magnetic field generator and the affected tissues does not necessarily have to be strictly managed; and if it were necessary to secure the magnetic flux density of 21 mT or more, it would be preferable that the magnetic field generator and the affected tissues be placed opposite each other to apply the magnetic field to the affected tissues in an area of 5 mm or less from the inner diameter face of the coil.

Measurement Conditions for Magnetic Flux Density

Simulation Software: JMAG Designer 14.1
Solver: 3D FEM (Finite Element Method)
Simulation Type: Magnetic Field Analysis (Frequency Response)

2. Confirmation of Cancer Cell Cytostatic Effect

The cancer cell cytostatic effect of Example 1 was observed with respect to normal cells and cancer cells. The application was performed by placing a petri dish, in which the relevant cells were sowed, inside the helical part of the coil.

2.1 Normal Cells

Figure 7:
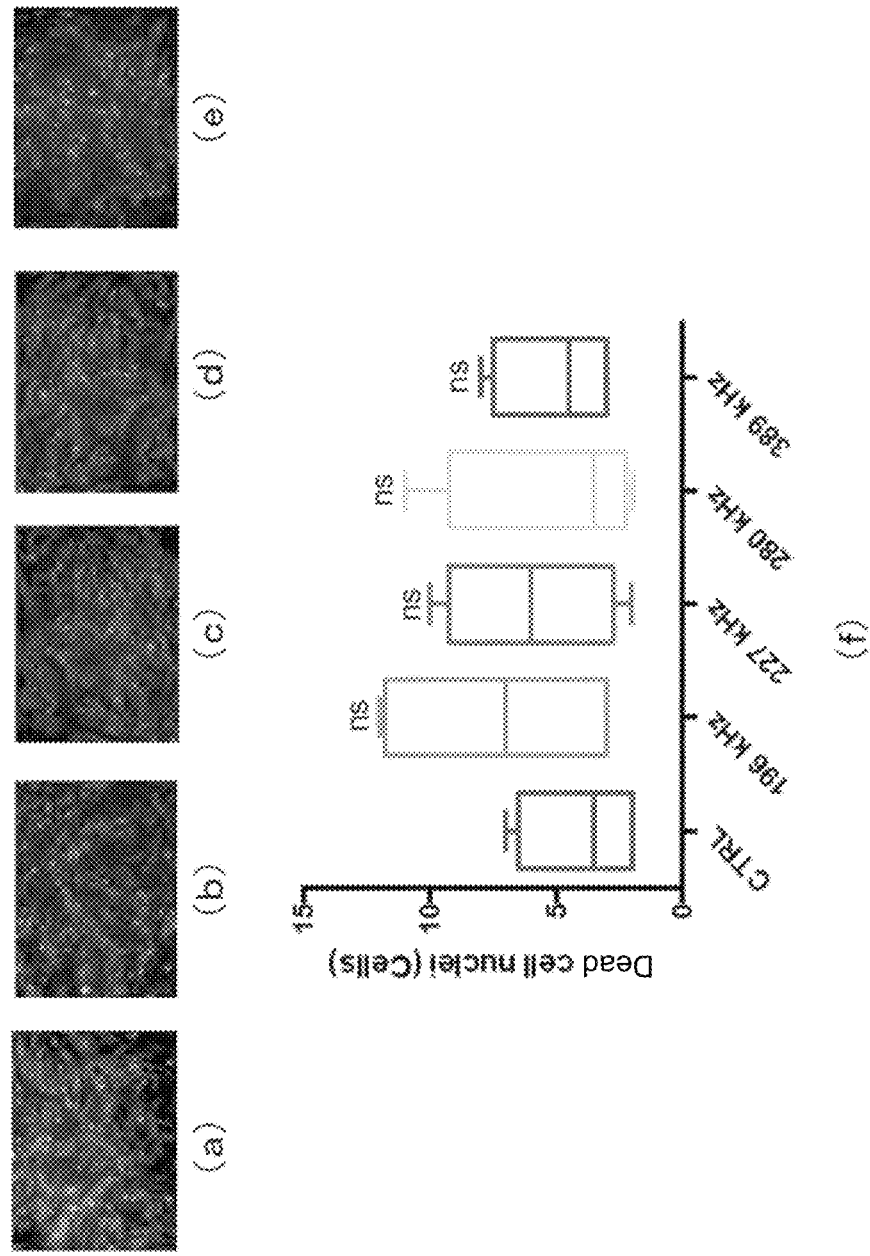
FIG. 7 shows observation results of normal cells to which the example of the present invention is applied.

FIG. 7 shows observation results of human stellate cells (NHA cells) as normal cells to which Example 1 was applied. Cells purchased from Lonza group, Ltd. were used as the human stellate cells. FIG. 7(a) is an image captured when cell culture was performed for 24 hours without applying the alternating magnetic field (Comparative Example 1-07a). FIG. 7(b) is an image captured when the cell culture was performed for 24 hours after applying the alternating magnetic field at the frequency of 196 kHz for 30 minutes (Example 1-07b). FIG. 7(c) to FIG. 7(e) (Example 1-07c to Example 1-07e) are images captured by changing only the frequency in the condition for FIG. 7(b) to 227 kHz, 280 kHz, and 389 kHz, respectively. In each of Example 1-07b to Example 1-07e and Comparative Example 1-07a, Culture Condition 1 described below was used to culture the cells. The images of FIG. 7(a) to FIG. 7(e) were captured by a fluorescence microscope NIKON TE2000E.

Culture Condition 1

Dyed $1\times10^5$ cells/4-cm dish using Calcein-AM by Sigma (to dye living cells) and propidium iodide (to dye nuclei and check dead cells) were sowed and cultured for 24 hours.

FIG. 7(f) is a graph showing an analysis result of the number of dead cells after the cell culture. The number of dead cells is the count number of cells by the fluorescence microscope. Five pieces of data indicated in FIG. 7F correspond to FIG. 7(a) to FIG. 7(e), respectively. Specifically, the first "CTRL" is data based on the cell culture (Comparative Example 1-07a) explained about FIG. 7(a); the second "196 kHz" is data based on the cell culture (Example 1-07b) explained about FIG. 7(b); the third "227 kHz" is data based on the cell culture (Example 1-07c) explained about FIG. 7(c); the fourth "280 kHz" is data based on the cell culture (Example 1-07d) explained about FIG. 7(d); and the fifth "389 kHz" is data based on the cell culture (Example 1-07e) explained about FIG. 7(e).

No significant cytostatic effect could not be confirmed as illustrated in FIG. 7 even by using Example 1 on the human stellate cells (the normal cells). Consequently, this result successfully confirmed that the effect of suppressing the proliferation of the normal cells by the present invention was very low as compared to the cancer cell cytostatic effect.

2.2 Cancer Cells

Experiments to check the cancer cell cytostatic effect of the present invention of Example 1 regarding the cancer cells were conducted about human glioblastoma cells (U87), human malignant melanoma cells (SK-MEL-24), human tongue cancer (squamous cell neoplasm) cells (OSC-19), human breast cancer cells (MCF7), and human epithelial cell line derived from a lung carcinoma tissue (A549). An alternating magnetic field transistor inverter (Hot Shot, Ameritherm Inc., New York, U.S.A.) was used in the confirmatory experiments. The coil was as described earlier.

2.2.1 Human Glioblastoma Cells (U87)

Figure 8:
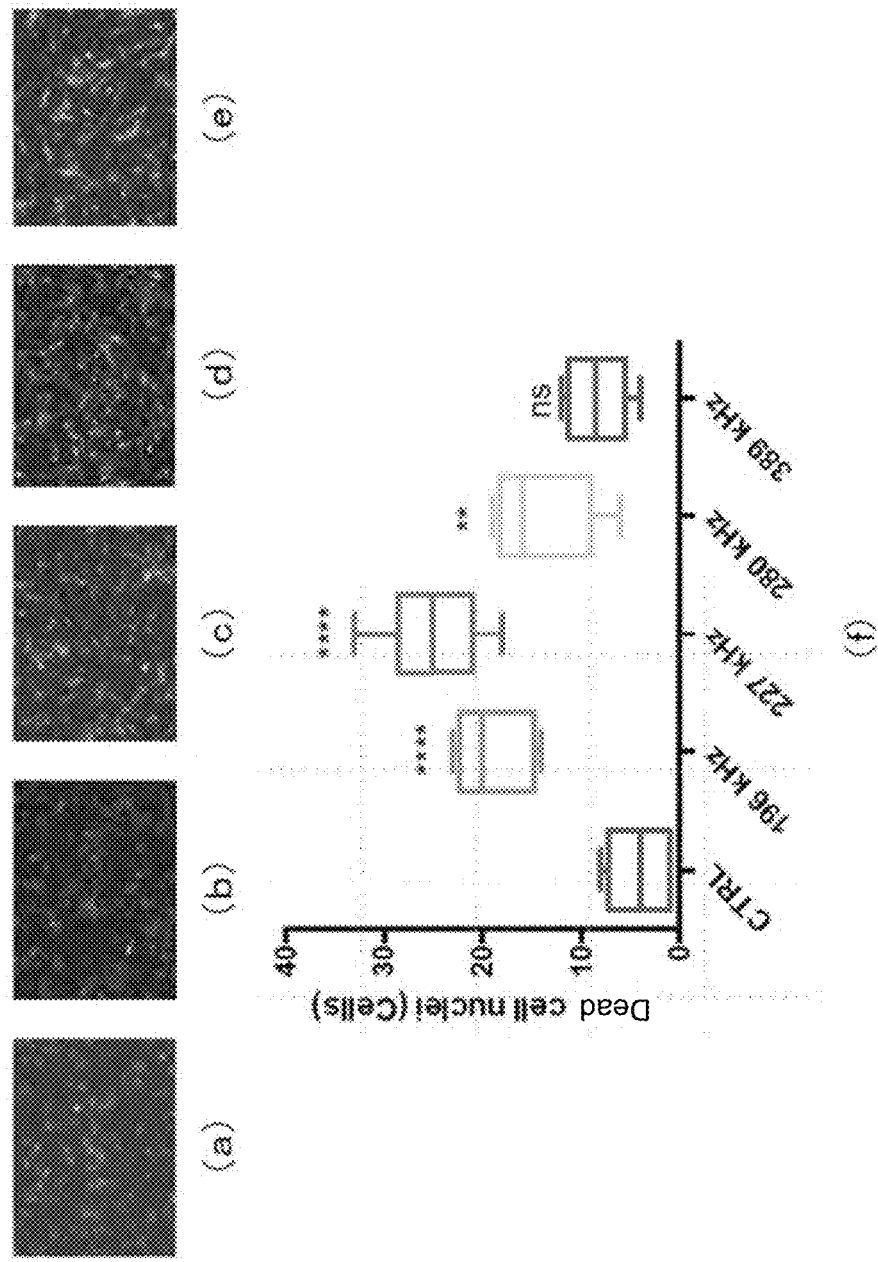
FIG. 8 shows observation results of a cancer cell cytostatic effect according to the example of the present invention.

FIG. 8 shows observation results of the cytostatic effect by Example 1 with respect to the human glioblastoma cells (U87). Human GB cell line U87 cells purchased from American Type Culture Collection (ATCC) (Virginia, U.S.A.) were used as the human glioblastoma cells (U87). FIG. 8(a) is an image captured when the cell culture was performed without applying the alternating magnetic field (Comparative Example 1-08a). FIG. 8(b) is an image captured when the cell culture was performed after applying the alternating magnetic field at the frequency of 196 kHz for 30 minutes (Example 1-08b). FIG. 8(c) to FIG. 8(e) (Example 1-08c to Example 1-08e) are images captured by changing only the frequency in the condition for FIG. 8(b) to 227 kHz, 280 kHz, and 389 kHz, respectively. Culture Condition 1 was used to culture the cells and the images of FIG. 8(a) to FIG. 8(e) were captured by the fluorescence microscope NIKON TE2000E.

FIG. 8(f) is a graph showing an analysis result of the number of dead cells after the cell culture. Five pieces of data indicated in FIG. 8F correspond to FIG. 8(a) to FIG. 8(e), respectively. Specifically, the first "CTRL" is data based on the cell culture (Comparative Example 1-08a) explained about FIG. 8(a); the second "196 kHz" is data based on the cell culture (Example 1-08b) explained about FIG. 8(b); the third "227 kHz" is data based on the cell culture (Example 1-08c) explained about FIG. 8(c); the fourth "280 kHz" is data based on the cell culture (Example 1-08d) explained about FIG. 8(d); and the fifth "389 kHz" is data based on the cell culture (Example 1-08e) explained about FIG. 8(e). The number of dead cells was measured in the same manner as in the aforementioned case of the human stellate cells.

Regarding the human glioblastoma cells (U87), a significant increase of the number of dead cells was observed as illustrated in FIG. 8 by applying the magnetic field at the frequencies of 196 kHz (Example 1-08b), 227 kHz (Example 1-08c), and 280 kHz (Example 1-08d) using Example 1. Consequently, this result confirmed that the present invention had the effect of suppressing the proliferation of the human glioblastoma cells (U87).

2.2.2 Human Malignant Melanoma Cells (SK-MEL-24)

Figure 9:
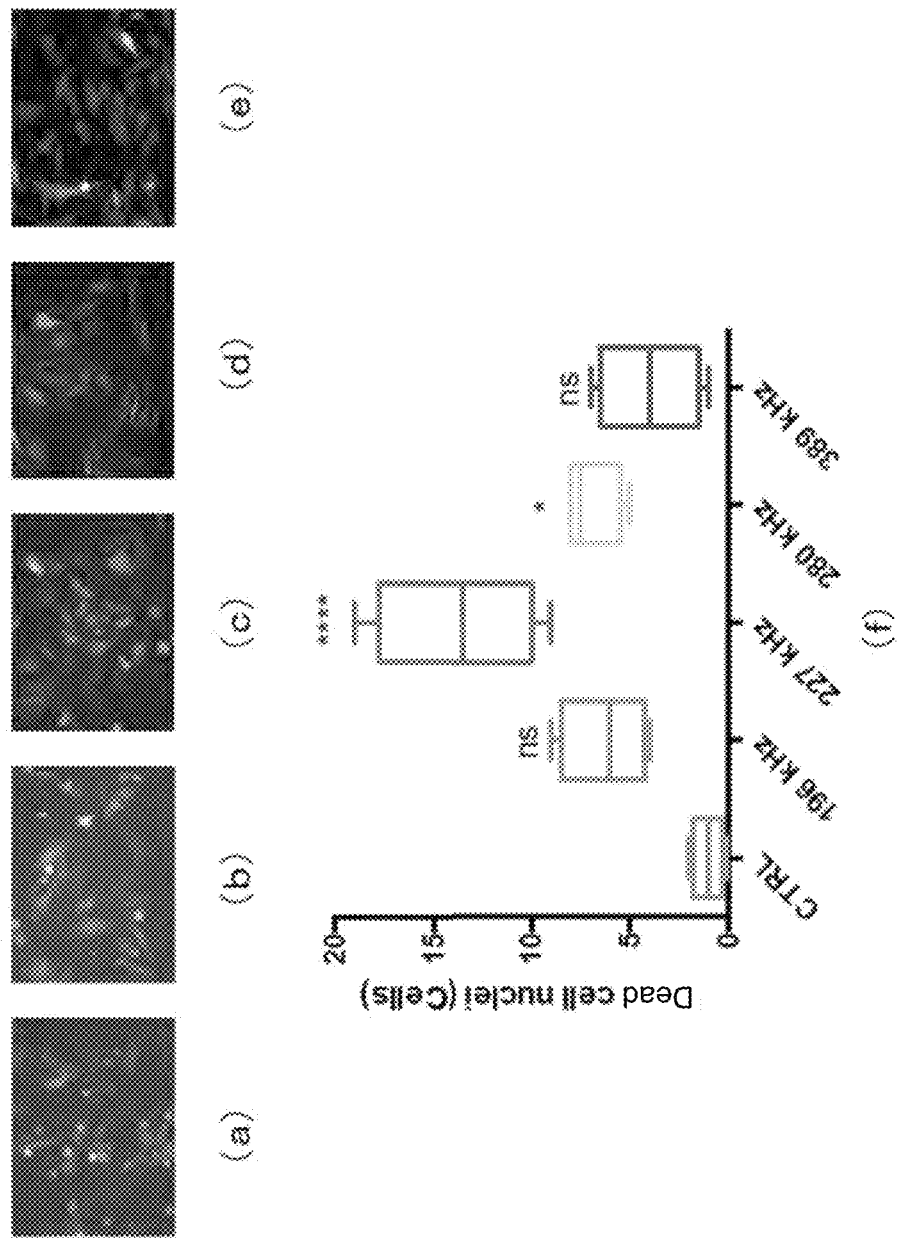
FIG. 9 shows observation results of the cancer cell cytostatic effect according to the example of the present invention.

FIG. 9 shows observation results of the cytostatic effect by Example 1 with respect to human malignant melanoma cells (SK-MEL-24). The human malignant melanoma cells (SK-MEL-24) purchased from ATCC were used. FIG. 9(a) is an image captured when the cell culture was performed without applying the alternating magnetic field (Comparative Example 1-09a). FIG. 9(b) to FIG. 9(e) are images captured respectively after applying the alternating magnetic field at the frequency of 196 kHz (Example 1-09b) for FIG. 9(b), at the frequency of 227 kHz (Example 1-09c) for FIG. 9(c), at the frequency of 280 kHz (Example 1-09d) for FIG. 9(d), and at the frequency of 389 kHz (Example 1-09e) for FIG. 9(e) for 30 minutes each time and then performing the cell culture. Culture Condition 1 was used to culture the cells and the images of FIG. 9(a) to FIG. 9(e) were captured by the fluorescence microscope NIKON TE2000E.

Five pieces of data indicated in FIG. 9(f) represent a graph indicating the analysis result of the number of dead cells after the culture corresponding to FIG. 9(a) to FIG. 9(e) (Comparative Example 1-09a and Example 1-09b to Example 1-09e), respectively. The number of dead cells was measured in the same manner as in the aforementioned case of the human stellate cells.

Regarding the human malignant melanoma cells (SK-MEL-24), a significant increase of the number of dead cells was observed as illustrated in FIG. 9 when the magnetic field was applied at the frequencies of 196 kHz (Example 1-09c), 227 kHz (Example 1-09d), and 280 kHz (Example 1-09e) using Example 1. This result confirmed that the present invention had the effect of suppressing the proliferation of the human malignant melanoma cells (SK-MEL-24).

2.2.3 Human Tongue Cancer (Squamous Cell Carcinoma) Cells (OSC-19)

Figure 10:
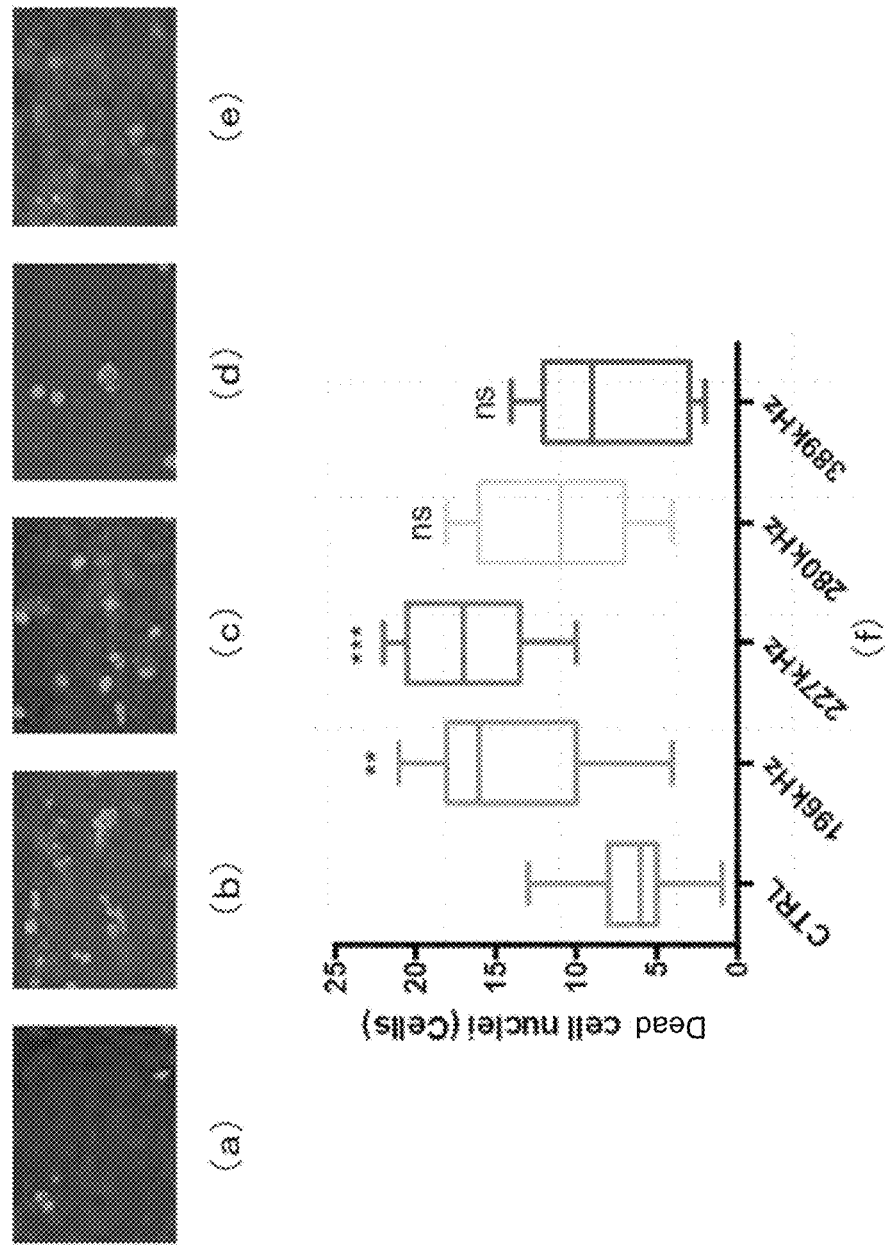
FIG. 10 shows observation results of the cancer cell cytostatic effect according to the example of the present invention.

FIG. 10 shows observation results of the cytostatic effect by Example 1 with respect to human tongue cancer (squamous cell carcinoma) cells (OSC-19). The human tongue cancer cells (OSC-19) purchased from The Health Science Research Resources Bank (Japan Health Sciences Foundation, Tokyo, Japan) were used. FIG. 10(a) is an image captured when the cell culture was performed without applying the alternating magnetic field (Comparative Example 1-10a). FIG. 10(b) to FIG. 10(e) are images captured respectively after applying the alternating magnetic field at the frequency of 196 kHz (Example 1-10b) for FIG. 10(b), at the frequency of 227 kHz (Example 1-10c) for FIG. 10(c), at the frequency of 280 kHz (Example 1-10d) for FIG. 10(d), and at the frequency of 389 kHz (Example 1-10e) for FIG. 10(e) for 30 minutes each time and then performing the cell culture. Culture Condition 1 was used to culture the cells and FIG. 10(a) to FIG. 10(e) were captured by the fluorescence microscope NIKON TE2000E.

Five pieces of data indicated in FIG. 10(e) represent a graph indicating the analysis result of the number of dead cells after the culture corresponding to FIG. 10(a) to FIG. 10(e) (Comparative Example 1-10a and Example 1-10b to Example 1-10e), respectively. The number of dead cells was measured in the same manner as in the aforementioned case of the human stellate cells.

Regarding the human tongue cancer cells (OSC-19) a significant increase of the number of dead cells was observed as illustrated in FIG. 10 when the magnetic field was applied at the frequencies of 196 kHz (Example 1-10b) and 227 kHz (Example 1-10c) using Example 1. This result confirmed that the present invention had the effect of suppressing the human tongue cancer cells (OSC-19).

2.2.4 Human Breast Cancer Cells (MCF7)

Figure 11:
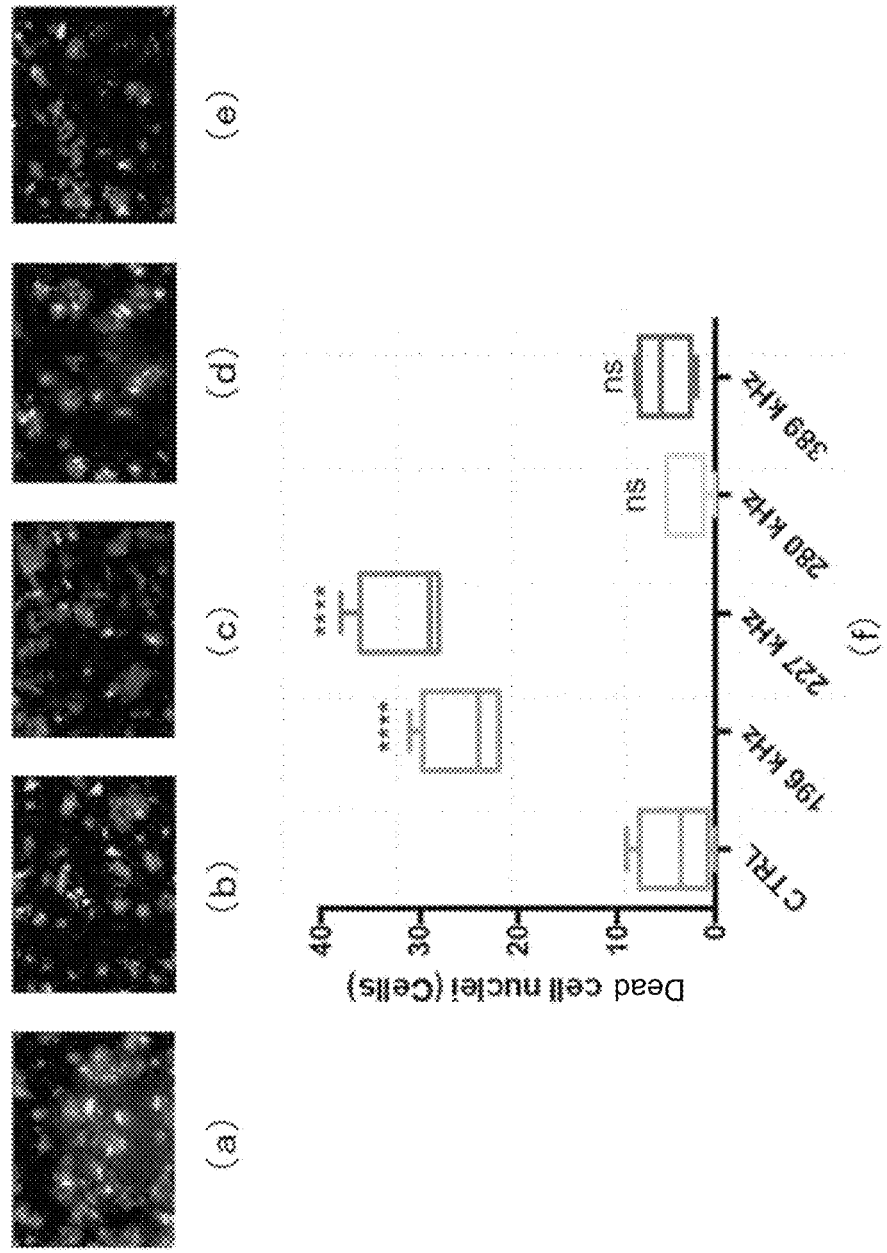
FIG. 11 shows observation results of the cancer cell cytostatic effect according to the example of the present invention.

FIG. 11 shows observation results of the cytostatic effect by Example 1 with respect to human breast cancer cells (MCF7). The human breast cancer cells (MCF7) purchased from ATCC were used. FIG. 11(a) is an image captured when the cell culture was performed without applying the alternating magnetic field (Comparative Example 1-11b). FIG. 11(b) to FIG. 11(e) are images captured respectively after applying the alternating magnetic field at the frequency of 196 kHz (Example 1-11b) for FIG. 11(b), at the frequency of 227 kHz (Example 1-11c) for FIG. 11(c), at the frequency of 280 kHz (Example 1-11d) for FIG. 11(d), and at the frequency of 389 kHz (Example 1-11e) for FIG. 11(e) for 30 minutes each time and then performing the cell culture. Culture Condition 1 was used to culture the cells and the images of FIG. 11(a) to FIG. 11(e) were captured by the fluorescence microscope NIKON TE2000E.

Five pieces of data indicated in FIG. 11(f) represent a graph indicating the analysis result of the number of dead cells after the culture corresponding to FIG. 11(a) to FIG. 11(e) (Comparative Example 1-11a and Example 1-11b to Example 1-11e). The number of dead cells was measured in the same manner as in the aforementioned case of the human stellate cells.

Regarding the human breast cancer cells (MCF7), a significant increase of the number of dead cells was observed as illustrated in FIG. 11 when the magnetic field was applied at the frequencies of 196 kHz (Example 1-11c) and 227 kHz (Example 1-11d) using Example 1. This result confirmed that the present invention had the effect of suppressing the proliferation of the breast cancer cells (MCF7).

2.2.5 Human Epithelial Cell Line Derived from a Lung Carcinoma Tissue (A549)

Figure 20:
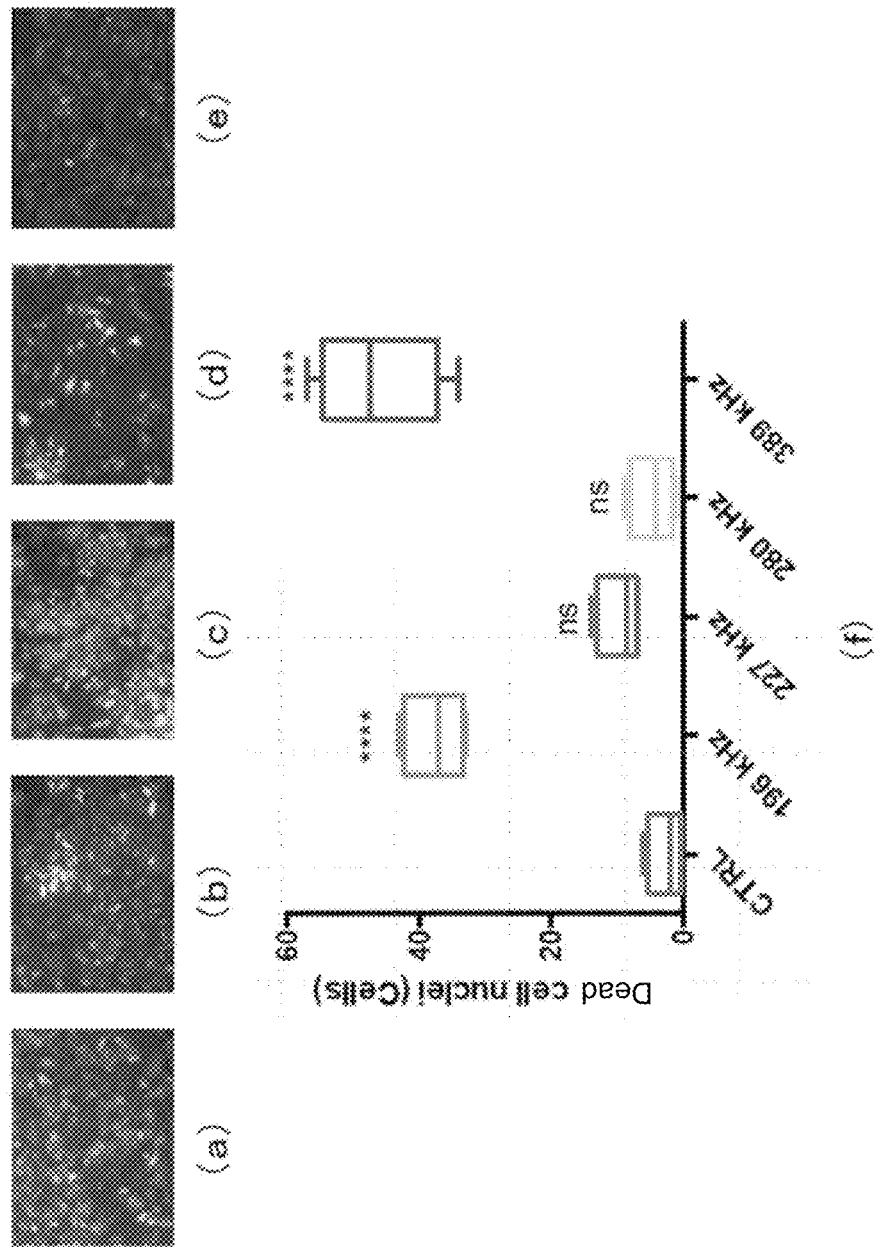
FIG. 20 shows observation results of the cancer cell cytostatic effect according to the example of the present invention.

FIG. 20 shows observation results of the cytostatic effect by Example 1 with respect to human epithelial cell line derived from a lung carcinoma tissue (A549). The human epithelial cell line derived from a lung carcinoma tissue (A549) purchased from ATCC were used. FIG. 20(a) is an image captured when the cell culture was performed without applying the alternating magnetic field (Comparative Example 1-20a). FIG. 20(b) to FIG. 20(e) are images captured respectively after applying the alternating magnetic field at the frequency of 196 kHz (Example 1-20b) for FIG. 20(b), at the frequency of 227 kHz (Example 1-20c) for FIG. 20(c), at the frequency of 280 kHz (Example 1-20d) for FIG. 20(d), and at the frequency of 389 kHz (Example 1-20e) for FIG. 20(e) for 30 minutes each time and then performing the cell culture. Culture Condition 1 was used to culture the cells and the images of FIG. 20(a) to FIG. 20(e) were captured by the fluorescence microscope NIKON TE2000E.

Five pieces of data indicated in FIG. 20(a) show a graph indicating the analysis result of the number of dead cells after the culture corresponding to FIG. 20(a) to FIG. 20(e) (Comparative Example 1-20a and Example 1-20b to Example 1-20e), respectively. The number of dead cells was measured in the same manner as in the aforementioned case of the human stellate cells.

Regarding the human epithelial cell line derived from a lung carcinoma tissue (A549), a significant increase of the number of dead cells was observed as illustrated in FIG. 20 when the magnetic field was applied at the frequencies of 196 kHz (Example 1-20b) and 389 kHz (Example 1-20e) using Example 1. This result confirmed that the present invention had the effect of suppressing the proliferation of the human epithelial cell line derived from a lung carcinoma tissue (A549).

The proliferation of the cancer cells is suppressed by applying the magnetic field at a specific frequency corresponding to the cancer type. Particularly, the present invention which has been illustrated by the examples above can exert the excellent cancer cell cytostatic effect through a combination of the specific frequency and the application duration. Accordingly, not only the cancer cell cytostatic effect is enhanced, but also the reduction of the user's burden is realized by setting the cancer type parameter, which is the combination of the specific frequency and the application duration, and thereby making it possible to easily apply a specified magnetic field. Therefore, the present invention should preferably be configured to store such a parameter, which is the combination of the specific frequency and the application duration, in the memory by associating the parameter with the cancer type. Consequently, an input to the cancer type input unit evokes an arbitrary cancer type parameter, which is set as a desired cancer type parameter, and the electric current is supplied to the magnetic field generator based on a set value. As a result, the present invention can generate an appropriate magnetic field to achieve the cytostatic effect for the desired cancer type and can easily achieve the cancer cell cytostatic effect by applying the magnetic field.

2.3 Influence of Magnetic Field Application on Cell Division of Cancer Cells FIG. 12 shows observation results of a cell division state of the human glioblastoma cells (U87). FIG. 12(a) is an image captured when the human glioma cells (U87) were cultured without applying the magnetic field (Comparative Example 1-12a). FIG. 12(b) is an image captured after applying the alternating magnetic field at the frequency of 227 kHz for 30 minutes by using Example 1 and then culturing the cells (Example 1-12b). Culture Condition 1 was used to culture the cells and the images were captured by using the fluorescence microscope.

When the cells were cultured without applying the magnetic field (Comparative Example 1-12a), the cell division was observed at positions indicated with white arrows as shown in FIG. 12(a). On the other hand, when the cells were cultured after applying the magnetic field (Example 1-12b) as in FIG. 12(b), it was successfully observed that no cell division occurred. Based on this observation result, it was possible to infer that the cell division of the human glioblastoma cells (U87) would be inhibited by using the present invention.

2.4 Influence of Magnetic Field Application on Cancer Cells

Figure 13:
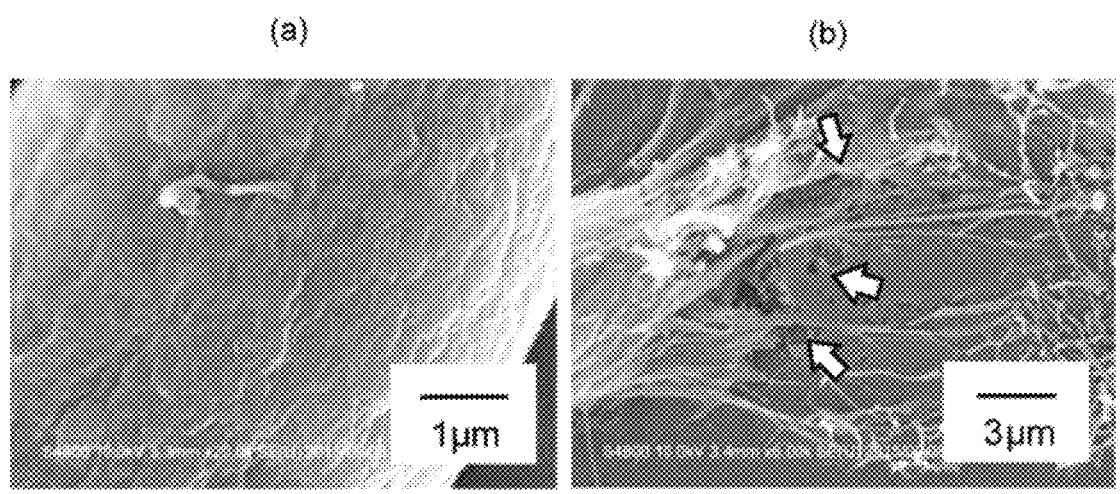
FIG. 13 shows observation results of the cancer cells to which the example of the present invention is applied.

FIG. 13 shows scanning electron micrographs of the human glioblastoma cells (U251). FIG. 13(a) is an image captured when the human glioblastoma cells (U251) were cultured without applying the magnetic field by using Example 1 (Comparative Example 1-13a). FIG. 13(b) is an image captured when the cells were cultured under Culture Condition 1 after applying the magnetic field at the frequency of 227 kHz for 30 minutes by using Example 1 (Example 1-13b). As a result of comparison between FIG. 13(a) and FIG. 13(b), it was successfully observed as indicated with white arrows in FIG. 13(b) that holes are made in the cell surfaces of Example 1-1301. Based on this observation result, it was possible to infer that cell surface membranes of the human glioblastoma cells (U251) could be damaged by using the present invention.

2.5 Temperature Change of Cancer Cells by Magnetic Field Application

A subcutaneous tumor model was prepared by transplanting the human glioblastoma cells (U87) at $5 \times 10^6$/mouse under the skin of a femoral region of a female 5-week-old Balb-c nude mouse. A transplanted area of the tumor model was placed opposite the magnetic field generator of Example 1 and the magnetic field was applied to the transplanted area, and changes in the temperature of the tumor model were observed. The application of the magnetic field was performed at the frequency of 227 kHz for 30 minutes.

Figure 14:
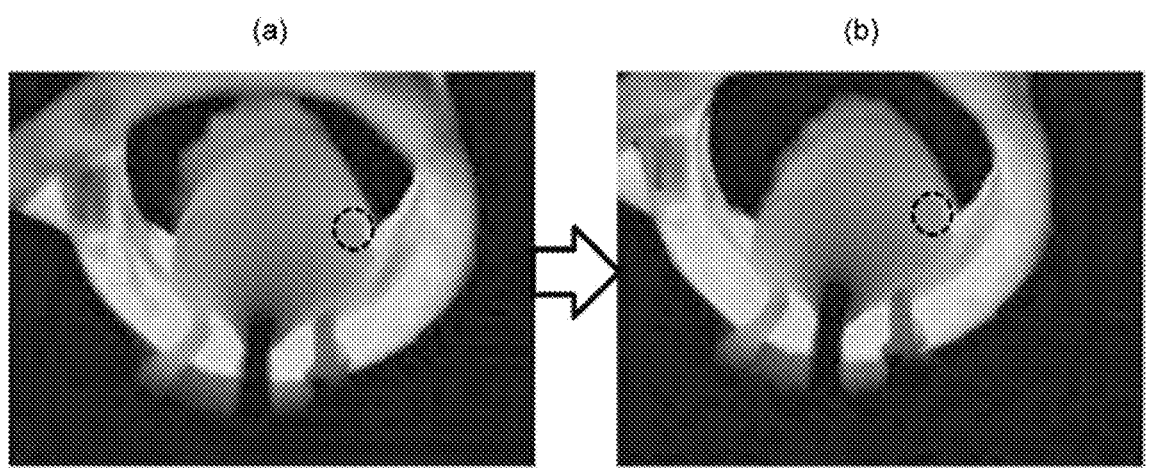
FIG. 14 shows observation results of a tumor model to which the example of the present invention is applied.

FIG. 14 shows observation results of the above-described tumor model. Referring to FIG. 14, an area with stronger whiteness has a higher temperature, so that changes in the temperature of the tumor model as caused by the application of the magnetic field by using Example 1 can be observed. The temperature was judged from image capture results by means of thermography. FIG. 14(a) is a temperature measurement result of the tumor model before the application. Regarding FIG. 14(a), the temperature in the image was from 24° C. to 37.5° C. FIG. 14(b) is a temperature measurement result of the tumor model after the application. The highest temperature in the image was 36.1° C. and the temperature of the affected tissues surrounded by a broken line was 34.5° C. Specifically speaking, even when the magnetic field is applied by using the present invention, the temperature of the cancer cells does not reach the temperature range of 40° C. to 43° C., which is well-known as the cancer cell killing temperature. Therefore, it was possible to infer that the possibility for the cancer cell cytostatic effect according to the present invention to be caused by killing of the cancer cells with hot heat would be low.

2.6 Confirmation of Tumor Proliferation Suppressing Effect

Tumor models of the human tongue cancer (squamous cell carcinoma) cells (OSC-19), the human glioblastoma cells (U87), the human breast cancer (MDAMB231), the human pancreatic cancer cells (PANC1), and the human the malignant mesothelioma cells (Meso-1) were prepared respectively and the tumor proliferation suppressing effect by the application of the magnetic field using Example 1 was checked. Enlargement of the tumor was evaluated based on a volume change. Regarding the volume of the tumor, the tumor size of each individual of the tumor model was measured with a vernier caliper and a value obtained by converting the tumor size into the volume according to Expression (1) and Expression (2) was defined as the tumor volume.

$$\text{Tumor volume } (TV)(\text{mm}^3) = \text{length} \times (\text{width})^2/2 \quad (1)$$

$$\text{Rate of tumor volume } (\%) = TV/TV_{(day1)} \times 100 \quad (2)$$

2.6.1 Tumor of Human Tongue Cancer (Squamous Cell Carcinoma) Cells (OSC-19)

The human tongue cancer (squamous cell carcinoma) cells (OSC-19) were transplanted at $1 \times 10^6$/mouse under the skin of a femoral region of a female 5-week-old Balb-c nude mouse in order to prepare subcutaneous tumor models using immunodeficient mice. The population was divided into two groups and the magnetic field was applied to individuals belonging to a first group by using Example 1. The first group was defined as an AMF group (Example 1-1501). The alternating magnetic field was applied to the tumor of the AMF group (Example 1-1501) at the frequency of 227 kHz for 30 minutes per day for consecutive five days from the 1st day to the 5th day by setting the next day of the transplantation as the 1st day. No application was performed for individuals belonging to the second group. The second group was defined as a Control group (Comparative Example 1-1500). The tumor size of each individual belonging to the AMF group (Example 1-1501) and the Control group (Comparative Example 1-1500) was measured every day and was converted into the tumor volume according to Expression (1) and Expression (2).

Figure 15:
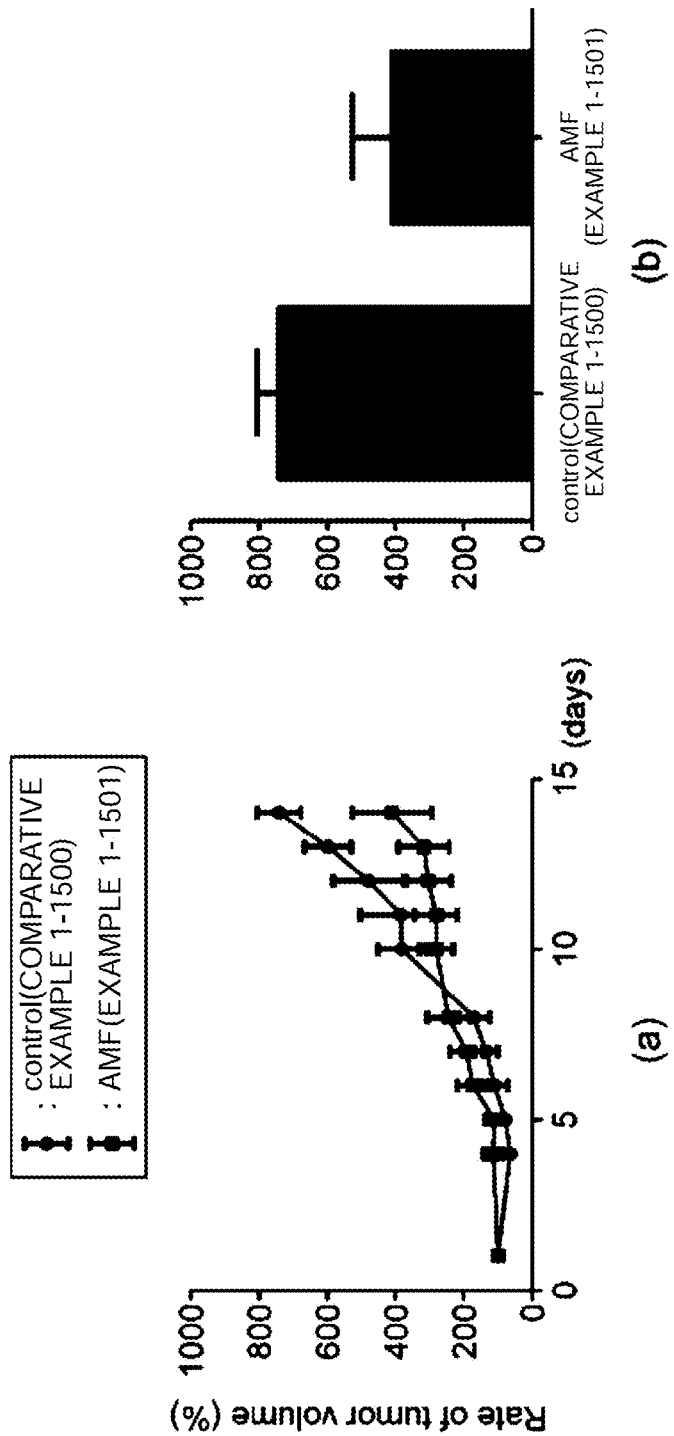
FIG. 15 shows observation results of changes in a tumor volume according to the example of the present invention.

FIG. 15 shows observation results of changes in the tumor volume of the human tongue cancer (squamous cell carcinoma) cells (OSC-19). Exponentiation was performed by setting the tumor volume of the AMF group (Example 1-1501) and the Control group (Comparative Example 1-1500) on the 1st day as 100 and FIG. 15(a) shows changes in the volume for 15 days from the next day of the transplantation (the 1st day) with respect to AMF (Example 1-1501) and Control (Comparative Example 1-1500) by using exponentiated volume values. As indicated in FIG. 15(a), the AMF group (Example 1-1501) was confirmed to have a tendency that enlargement of their tumor volume on the 10th day was suppressed as compared to the Control group (Comparative Example 1-1500). An enlargement rate of the tumor of Control (Comparative Example 1-1500) on the 10th day was 381%. On the other hand, the enlargement rate of the tumor of AMF (Example 1-1501) was 281%. As indicated in FIG. 15(a), the enlargement rate of the tumor of Control (Comparative Example 1-1500) on the 15th day was 741%. On the other hand, the enlargement rate of the tumor of AMF (Example 1-1501) was 411%.

Referring to FIG. 15(b), the volume on the 14th day exponentiated by defining the volume on the 1st day as indicated in FIG. 15(a) as 100% and the enlargement of the tumor volume of Control (Comparative Example 1-1500) was compared with that of AMF (Example 1-1501). As indicated in FIG. 15(b), the enlargement rate of the tumor of Control (Comparative Example 1-1500) was 770%. On the other hand, the enlargement rate of the tumor of AMF (Example 1-1501) was 400%. This result successfully confirmed that the effect of suppressing the tumor proliferation of the tongue cancer (squamous cell carcinoma) continued for at least 14 days by using the present invention.

2.6.2 Tumor of Human Glioblastoma Cells (U87)

FIG. 16 shows observation results of changes in the tumor volume of the human glioblastoma cells (U87). The human glioblastoma cells (U87) purchased from ATCC were used. Subcutaneous tumor models were prepared by transplanting the human glioblastoma cells U87 at $5 \times 10^6$/mouse under the skin of a femoral region of each female 5-week-old Balb-c nude mouse. The population was divided into three groups and the magnetic field was applied to individuals belonging to a first group once on the transplantation day (the 0th day) by using Example 1. The first group was decided as Example 1-1601. The magnetic field was applied to individuals belonging to a second group for consecutive 5 days from the 0th day by using Example 1. The second group was decided as Example 1-1605. The magnetic field was applied once per day for Example 1-1601 and Example 1-1605 and in either case the frequency was 227 kHz and the application duration was 30 minutes. The magnetic field was not applied to individuals belonging to a third group. The third group was decided as Comparative Example 1-1600. The tumor size of each individual belonging to Example 1-1601, Example 1-1605, and Comparative Example 1-1600 was measured every day for consecutive 14 days from the transplantation day (the 0th day) with the vernier caliper and was converted into the volume according to Expression (1) and Expression (2). FIG. 16(a) is a captured image of individuals belonging to Example 1-1601, Example 1-1605, and Comparative Example 1-1600 on the 14th day. Referring to FIG. 16(a), the inside of an area surrounded by a solid line is an affected part of each of the examples and the comparative example. Regarding the tumor size indicated within the solid line in FIG. 16(a), Comparative Example 1-1600 was the largest, Example 1-1601 was smaller than Comparative Example 1-1600, and Example 1-1605 was the smallest.

FIG. 16(b) is a graph indicating changes in the tumor volume of Example 1-1601, Example 1-1605, and Comparative Example 1-1600 through exponentiation by setting the volume on the 0th day as 100%. As indicated in FIG. 16(b), the tumor enlargement rate of Comparative Example 1-1600 after the $0^{th}$ day relative to the volume on the 0th day is 100% or more; and the volume enlargement tendency clearly appeared as days elapsed. On the other hand, the tumor enlargement rate of Example 1-1601 relative to the volume on the 0th day changed to 84.8% (the 2nd day), 105% (the 4th day), and 89.75% (the 7th day). Furthermore, the enlargement rate of Example 1-1605 relative to the volume on the 0th day changed to 84.55% (the 2nd day), 89.44% (the 4th day), and 66.42% (the 7th day). The enlargement tendency like Comparative Example 1-1600 was not observed with regard to the tumor volume of Example 1-1601 and Example 1-1605.

As a result of comparison of the changes in the tumor volume of each example and the comparative example indicated in FIG. 16(b), it was successfully confirmed that the present invention had the effect of suppressing the proliferation of the glioblastoma tumor volume. Furthermore, as a result of comparison between Example 1-1601 and Example 1-1605, the enlargement rate of Example 1-1605 was lower on every measurement day. These results successfully confirmed that when the magnetic field was applied once according to the present invention under the same application condition, the effect of suppressing the proliferation of the glioblastoma tumor volume was exerted better with a larger number of times of applications.

FIG. 16(b) shows measurement results from the 0th day to the 7th day, but the measurement also continued after the 7th day. FIG. 16(c) shows measurement results of the tumor volume of Example 1-1605 and Comparative Example 1-1600 from the 0th day to the 14th day. The tumor volume of Comparative Example 1-1600 was 152.8 mm$^3$ on the 0th day, 206.8 mm on the 2nd day, 295.8 mm$^3$ on the 4th day, 329.6 mm$^3$ on the 7th day, 328.7 mm$^3$ on the 9th day, 370.9 mm$^3$ on the 11th day, and 752.8 mm$^3$ on the 14th day. On the other hand, the tumor volume of Example 1-1605 was 181.5 mm$^3$ on the 0th day, 153.3 mm$^3$ on the 2nd day, 159.6 mm$^3$ on the 4th day, 117.8 mm$^3$ on the 7th day, 118.2 mm$^3$ on the 9th day, 147.3 mm$^3$ on the 11th day, and 271.3 mm$^3$ on the 14th day.

As indicated in FIG. 16(c), Example 1-1605 showed the significant cancer cell cytostatic effect on and after the 4th day and its significant difference from the volume of Comparative Example 1-1600 increased as days elapsed. The changes in the tumor volume of Example 1-1605 indicated in FIG. 16(c) successfully confirmed that the effect of suppressing the proliferation of glioblastoma tumor volume continued for at least 14 days by applying the magnetic field by using the present invention. It is also possible to infer that this effect would also continue after the 14th day.

The present invention has the continuous effect of suppressing the proliferation of the tumor volume even with one application of the magnetic field. Also, the substantivity of the tumor volume proliferation suppressing effect enhances as the number of times of applications is increased. As indicated in FIG. 16(b) and FIG. 16(c), when the magnetic field was applied once by using Example 1, the tumor volume proliferation suppressing effect continued for at least 7 days; and when the magnetic field was applied 5 times, the tumor volume proliferation suppressing effect continued for at least 14 days.

Therefore, the present invention may be configured so that the number of times of applications can be set by inputting the cancer type to the cancer type input unit. FIG. 17 shows an example of the cancer type input unit to which the parameter of the number of times of applications can be set. As illustrated in FIG. 17, the cancer type parameter is associated with the frequency, the application duration, and the number of times of applications which are stored in the memory; and specified frequency, application duration, and the number of times of applications can be set and the magnetic field can be applied appropriately by inputting a desired cancer type. FIG. 17 illustrates an example of the cancer type input unit in which modes for the magnetic field application for Example 1-1601 and Example 1-1605 can be set.

2.6.3 Tumor of Human Breast Cancer (MDAMB231)

A human breast cancer (MDAMB231) was transplanted at 5×10$^6$/mouse under the skin of a femoral region of a female 5-week-old Balb-c nude mouse in order to prepare subcutaneous tumor models using immunodeficient mice. The population was divided into two groups and the magnetic field was applied to individuals belonging to a first group a total of 10 times for consecutive 5 days after the transplantation (from the 7th day), two days with no application, and then again for consecutive 5 days by using Example 1. The first group was decided as an AMF group (Example 1-2101). The magnetic field was applied once per day for Example 1-2101; and regarding each one application, the frequency was 227 kHz and the application duration was 30 minutes. The magnetic field was not applied to individuals belonging to a second group. The second group was decided as a CTRL group (Comparative Example 1-2100). The tumor size of each individual belonging to the AMF group (Example 1-2101) and the CTRL group (Comparative Example 1-2100) was measured every day for consecutive 14 days after the transplantation (from the 7th day) with the vernier caliper and was converted into the volume according to Expression (1) and Expression (2).

Figure 21:
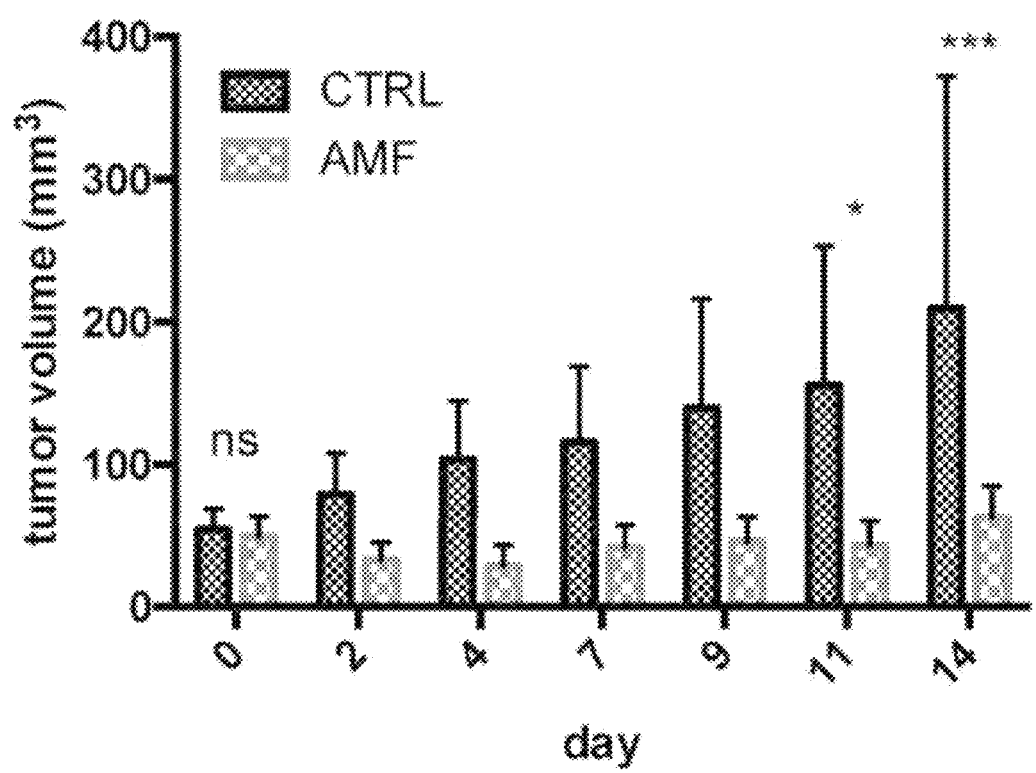
FIG. 21 shows observation results of changes in the tumor volume according to the example of the present invention.

FIG. 21 is a diagram which shows the enlargement of the tumor volume by comparing the CTRL group (Comparative Example 1-2100) with AMF (Example 1-2101). Regarding the CTRL group (Comparative Example 1-2100), the volume enlargement tendency clearly appeared as days elapsed. On the other hand, the volume of AMF (Example 1-2101) became smaller than, or stayed almost the same as, the 0th day. At any one of points in time, the tumor volume of AMF (Example 1-2101) was smaller than that of the CTRL group (Comparative Example 1-2100).

2.6.4 Tumor of Human Pancreatic Cancer Cells (PANC1)

Human pancreatic cancer cells (PANC1) were transplanted at 5×10$^6$/mouse under the skin of a femoral region of a female 5-week-old Balb-c nude mouse in order to prepare subcutaneous tumor models using immunodeficient mice. The population was divided into two groups and the magnetic field was applied to individuals belonging to a first group a total of 10 times for consecutive 5 days after the transplantation (from the 7th day), two days with no application, and then again for consecutive 5 days by using Example 1. The first group was decided as an AMF group (Example 1-2201). The magnetic field was applied once per day for Example 1-2201; and regarding each one application, the frequency was 227 kHz and the application duration was 30 minutes. The magnetic field was not applied to individuals belonging to a second group. The second group was decided as a CTRL group (Comparative Example 1-2200). The tumor size of each individual belonging to the AMF group (Example 1-2201) and the CTRL group (Comparative Example 1-2200) was measured every day for consecutive 14 days after the transplantation (from the 7th day) with the vernier caliper and was converted into the volume according to Expression (1) and Expression (2).

Figure 22:
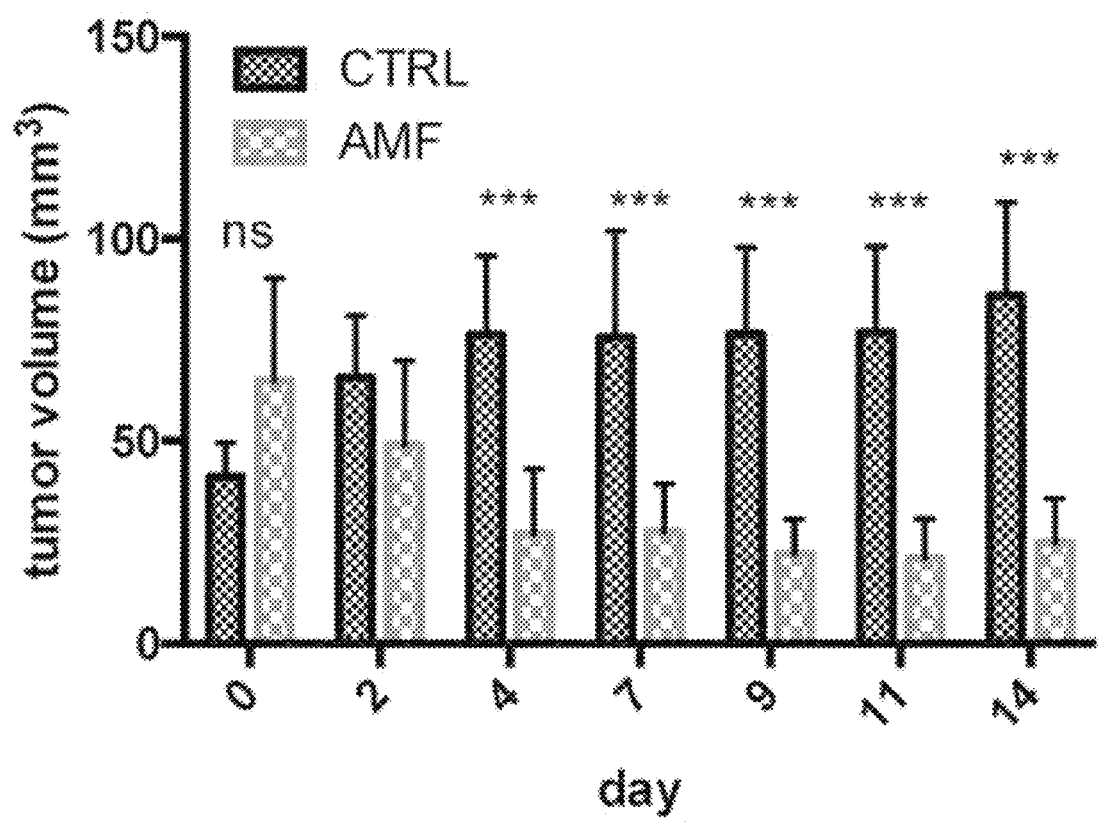
FIG. 22 shows observation results of changes in the tumor volume according to the working example of the present invention.

FIG. 22 is a diagram which shows the enlargement of the tumor volume by comparing the CTRL group (Comparative Example 1-2200) with AMF (Example 1-2201). Regarding the CTRL group (Comparative Example 1-2200), the volume enlargement tendency clearly appeared as days elapsed. On the other hand, the volume of AMF (Example 1-2201) continued decreasing as days elapsed.

2.6.5 Tumor of Human Glioblastoma Cells (U87) (Brain Tumor Models)

FIG. 18 shows observation results of brain tumor models of the human glioblastoma cells (U87). The operational advantages of the present invention were confirmed with fluorescent imaging and an overall survival rate of the tumor models as indicated in FIG. 18. The human glioblastoma cells (U87) purchased from ATCC were used. Firefly luciferase genes were transferred to the human glioblastoma cells by using Lentiviruses by a known gene recombination method and then the obtained cells were cultured under Culture Condition 1, thereby producing U87 cells transfected with a luciferase-encoding lentivirus. The brain tumor models were prepared by transplanting the U87 cells transfected with a luciferase-encoding lentivirus at $1\times10^6$/mouse to the brain of a female 5-week-old Balb-c nude mouse. Subsequently, D-luciferin was administered to the brain tumor models to make it possible to observe the tumor growth of U87 in the individuals. The observation terminated when the death of all the individuals was confirmed.

The population was divided into two groups and the magnetic field was applied to individuals belonging to a first group (the number of individuals: 6) by supplying an electric current of 250 A by using Example 1. The first group was decided as Example 1-1805. The magnetic field was applied once per day for Example 1-1805; and regarding each one application, the frequency was 227 kHz and the application duration was 30 minutes. The magnetic field was applied for consecutive 5 days from the 0th day (from the 0th day to the 4th day), no application was applied on the 5th day and the 6th day, and then the magnetic field was applied again from the 7th day to the 11th day. In other words, the magnetic field was applied to Example 1-1805 10 times. The magnetic field was not applied to individuals belonging to a second group (the number of individuals: 6). The second group was decided as Comparative Example 1-1800.

Fluorescent imaging of Example 1-1805 and Comparative Example 1-1800 was performed by using an ultrasensitive CCD camera and an image analysis equipment (equipment name: IVIS imaging system). The tumor proliferation suppressing effect was evaluated based on a value of the amount of luminescence (photons/second); and a smaller amount of luminescence was judged to have the tumor proliferation suppressing effect. One fluorescent image of the individuals belonging to Example 1-1805 and one fluorescent image of the individuals belonging to Comparative Example 1-1800 were extracted respectively and are shown in FIG. 18(a). FIG. 18(b) is a graph indicating changes in the amount of luminescence of Example 1-1805 and Comparative Example 1-1800. As indicated in FIG. 18(a) and FIG. 18(b), the amount of luminescence of Comparative Example 1-1800 increased as days elapsed. On the other hand, the amount of luminescence of Example 1-1805 did not show almost any increase even when days elapsed; and particularly on and after the 16th day, the amount of luminescence was little as compared to Comparative Example 1-1800 and a significant difference from Comparative Example 1-1800 was observed. Specifically speaking, it was successfully confirmed that Example 1 had the effect of suppressing the proliferation of the glioblastoma tumor also with respect to the brain tumor models.

Furthermore, FIG. 18(c) shows an overall survival rate of Example 1-1805 and Comparative Example 1-1800, which was calculated according to Expression (3).

$$\text{Overall Survival Rate (\%)} = \text{The Number of All Dead Individuals}/6\times100 \quad (3)$$

Regarding Comparative Example 1-1800 as indicated in FIG. 18(c), the first individual died on the 20th day and all the individuals died before and on the 28th day. The overall survival rate changed as follows: 83% on the 20th day, 66% on the 22th day, 33% on the 25th day, 16% on the 26th day, and 0% on the 28th day. On the other hand, regarding Example 1-1805, the first individual died on the 26th day and all the individuals died on the 35th day. The overall survival rate changed as follows: 83% on the 26th day, 50% on the 27th day, 33% on the 28th day, 16% on the 30th day, and 0% on the 35th day. It was successfully confirmed that the application of a specified magnetic field by using Example 1 would provide an excellent prognosis of the glioblastoma.

Figure 23:
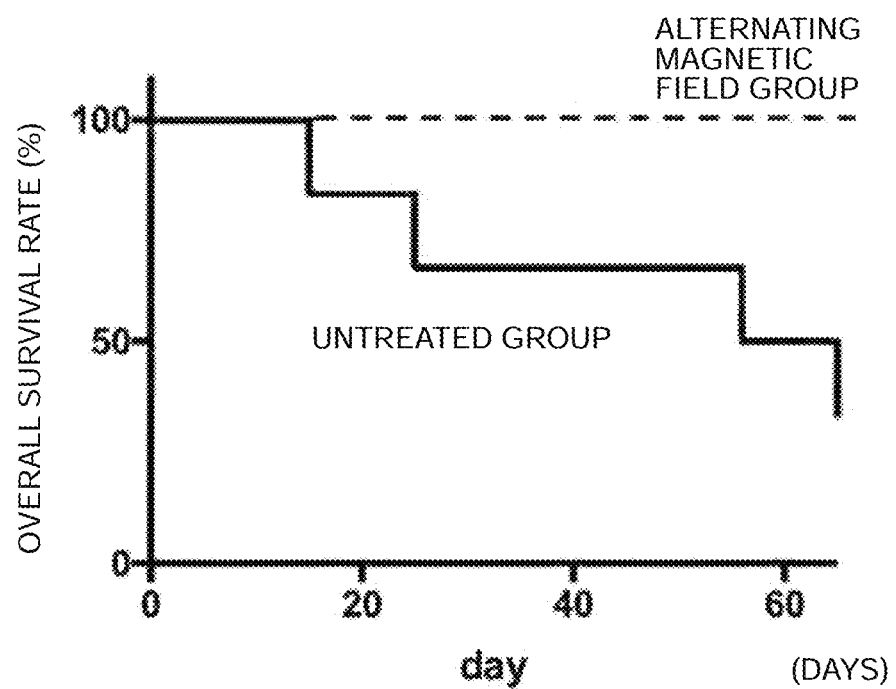
FIG. 23 shows observation results of an overall survival rate according to the example of the present invention.

Furthermore, human glioblastoma cells (U251) were used instead of the human glioblastoma cells (U87) and a similar observation was performed. Conditions other than the cell type are similar to those of the brain tumor models of the human glioblastoma cells (U87) as indicated in FIG. 18. The obtained overall survival rate is shown in FIG. 23. Regarding an untreated group to which the magnetic field was not applied, the overall survival rate decreased on and after the 16th day; however, regarding an alternating magnetic field group to which the magnetic field was applied, the overall survival rate of 100% was maintained even after 60 days elapsed. Therefore, it was successfully confirmed that the application of a specified magnetic field by using Example 1 would provide an excellent prognosis of the glioblastoma.

2.6.6 Tumor of Malignant Mesothelioma Cells (Meso-1)

Figure 19:
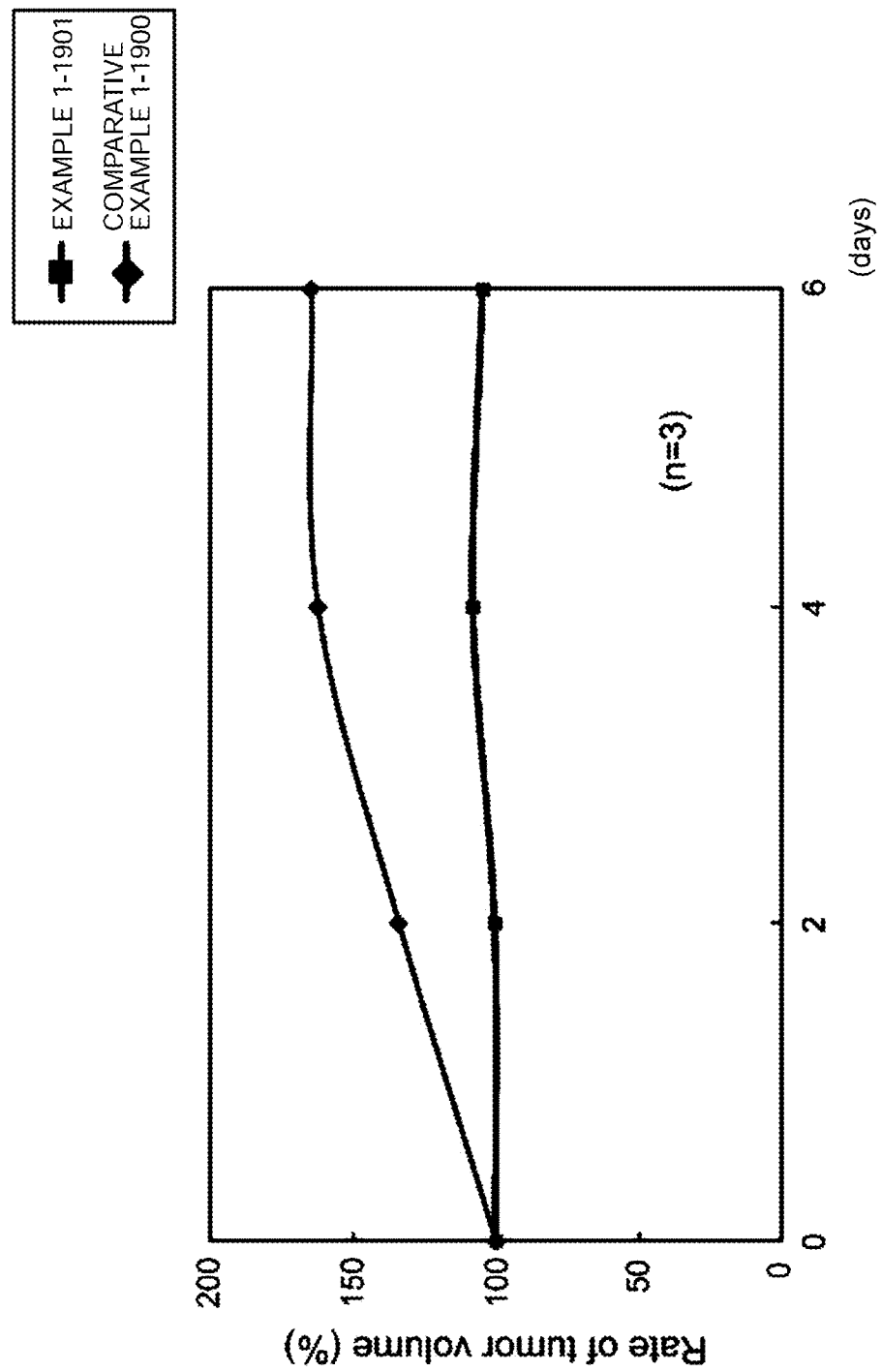
FIG. 19 shows observation results of changes in the tumor volume according to the example of the present invention.

FIG. 19 shows observation results of changes in the tumor volume of human malignant mesothelioma cells (Meso-1). The human malignant mesothelioma cells (Meso-1) purchased from ATCC were used. Subcutaneous tumor models were prepared by transplanting the human malignant mesothelioma cells (Meso-1) at $1\times10^6$/mouse under the skin of a buttock region of each female 5-week-old Balb-c nude mouse. The population was divided into two groups and the magnetic field was applied to individuals belonging to a first group on the transplantation day (the 0th day) by using Example 1. The first group was decided as Example 1-1901. The magnetic field was applied once for Example 1-1901 by supplying the electric current of 250 A at the frequency of 308 kHz during the application duration for 30 minutes. The magnetic field was not applied to individuals belonging to a second group. The second group was decided as Comparative Example 1-1900.

The tumor size of each individual belonging to Example 1-1901 and Comparative Example 1-1900 was measured on the transplantation day, the 2nd day, the 4th day, and the 6th day with the vernier caliper and was converted into the volume according to Expression (1) and Expression (2).

FIG. 19 is a graph indicating changes in the tumor volume of Example 1-1901 and Comparative Example 1-1900 through exponentiation by setting the volume on the 0th day as 100%. As indicated in FIG. 19, the tumor enlargement rate of Comparative Example 1-1900 after the $0^{th}$ day relative to the volume on the 0th day is 100% or more; and the volume enlarged as days elapsed. The enlargement rate of Comparative Example 1-1900 relative to the volume on the 0th day changed as follows: 134% (the 2nd day), 163% (the 4th day), and 164% (the 6th day). On the other hand, the enlargement rate of Example 1-1901 relative to the volume on the 0th day changed as follows: 100% (the 2nd day), 107% (the 4th day), and 104% (the 6th day). The enlargement tendency like Comparative Example 1-1900 was not observed with regard to the tumor volume of Example 1-1901. Accordingly, it was successfully confirmed that the present invention had the effect of suppressing the tumor proliferation of the malignant mesothelioma.

3. Side Effects

Side effects caused by the applications of the magnetic field by using the magnetic field generator of Example 1 were observed. Female 5-week-old Balb-c nude mice were divided into an AMF group to which the magnetic field was to be applied, and a CTRL group to which the magnetic field was to be not applied; and regarding each of the AMF group and the CTRL group, a group for transplanting a tumor under the skin and a group for transplanting the tumor inside the cranium were formed. The CTRL group will not be described below in detail, but corresponding individuals were prepared for the comparison with the AMF group. The AMF group to which the tumor was transplanted under the skin was further divided into a once-a-week group to which the magnetic field was applied once in a week, and a 5-times-a-week group to which the magnetic field was applied five times in a week; and an observation was performed after the elapse of 15 days after the transplantation. Specifically speaking, regarding the once-a-week group of the AMF group with the subcutaneous implant, the magnetic field was applied a total of twice; and regarding the 5-times-a-week group of the same AMF group, the magnetic field was applied a total of 10 times. Regarding the AMF group with the tumor transplanted within the cranium, the magnetic field was applied five times in a week, that is, a total of 40 times, and an observation was performed after the elapse of 90 days.

In any one of these cases, the magnetic field was applied for 30 minutes each time and the frequency was 227 kHz. The observation was performed via, for example, body weight measurement, blood drawing, and external observation; and specifically speaking, clinical signs, skin disorder, body weight, food intake, biological functions, kidney functions, panhemocytes, white blood cells, hemoglobin, blood platelets, and liver functions were evaluated.

FIG. 24 is a diagram indicating observation results of seven items, that is, clinical signs, skin disorder, a reduction of body weight, a reduction of food intake, degradation of biological functions, degradation of kidney functions, and a reduction of panhemocytes. However, regarding the reduction of the body weight, the reduction of the food intake, the degradation of the biological functions, the degradation of the kidney functions, and the reduction of the panhemocytes, whether a reduction or lowering of 20% or more from the CTRL group has occurred or not was observed. Regarding any one of these items, no side effects were observed as indicated in FIG. 24. Of the items indicated in FIG. 24, the body weight will be described in detail.

Figure 25:
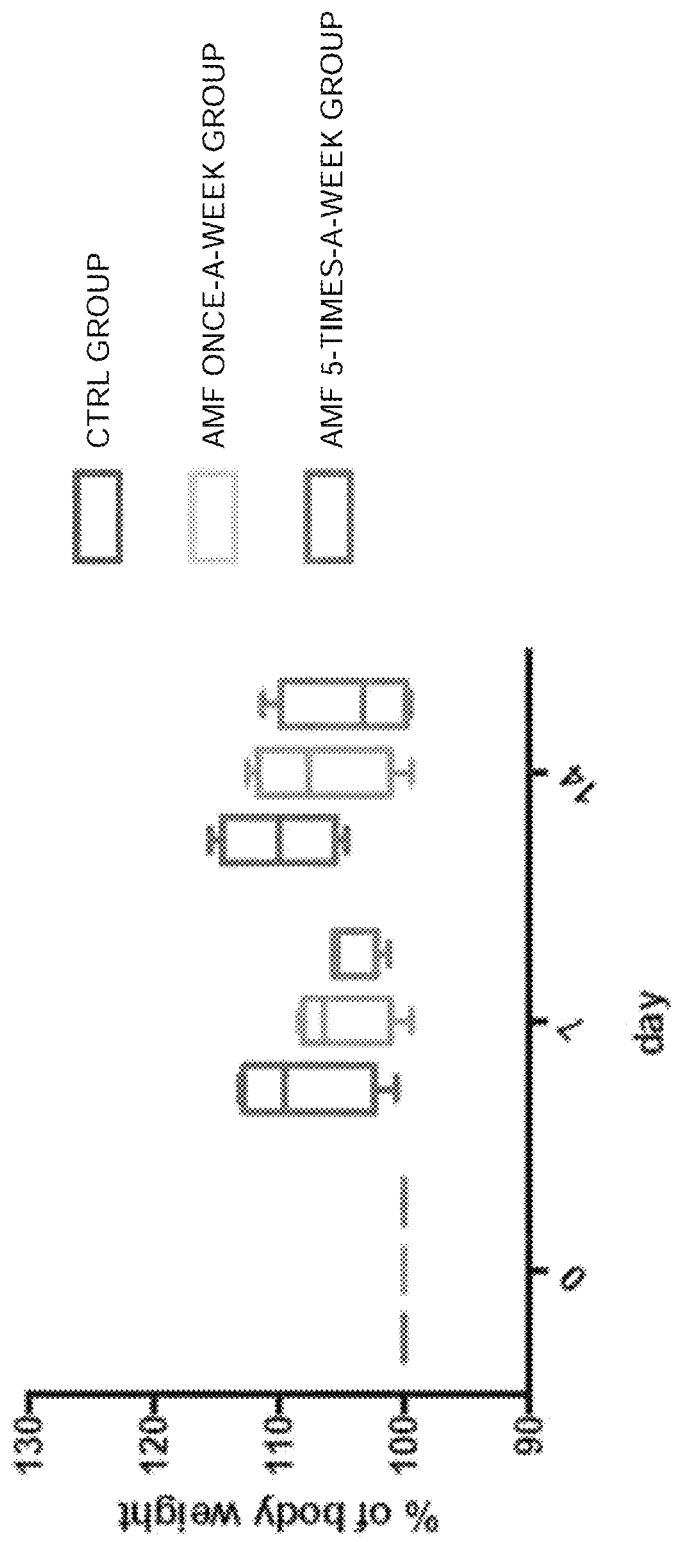
FIG. 25 shows observation results of the side effects according to the example of the present invention.

FIG. 25 is a diagram showing changes in the body weight 7 days later and 14 days later by setting the body weight on the observation start day as 100%. Regarding each observation result of 7 days later and 14 days later, data of the CTRL group, the once-a-week group of the AMF group, and the 5-times-a-week group of the AMF group are indicated from the left to the right. As indicated in FIG. 25, either one of the AMF groups had a small difference in the body weight from the CTRL group; and no reduction of 20% or more from the CTRL group can be seen as indicated in FIG. 24.

Figure 26:
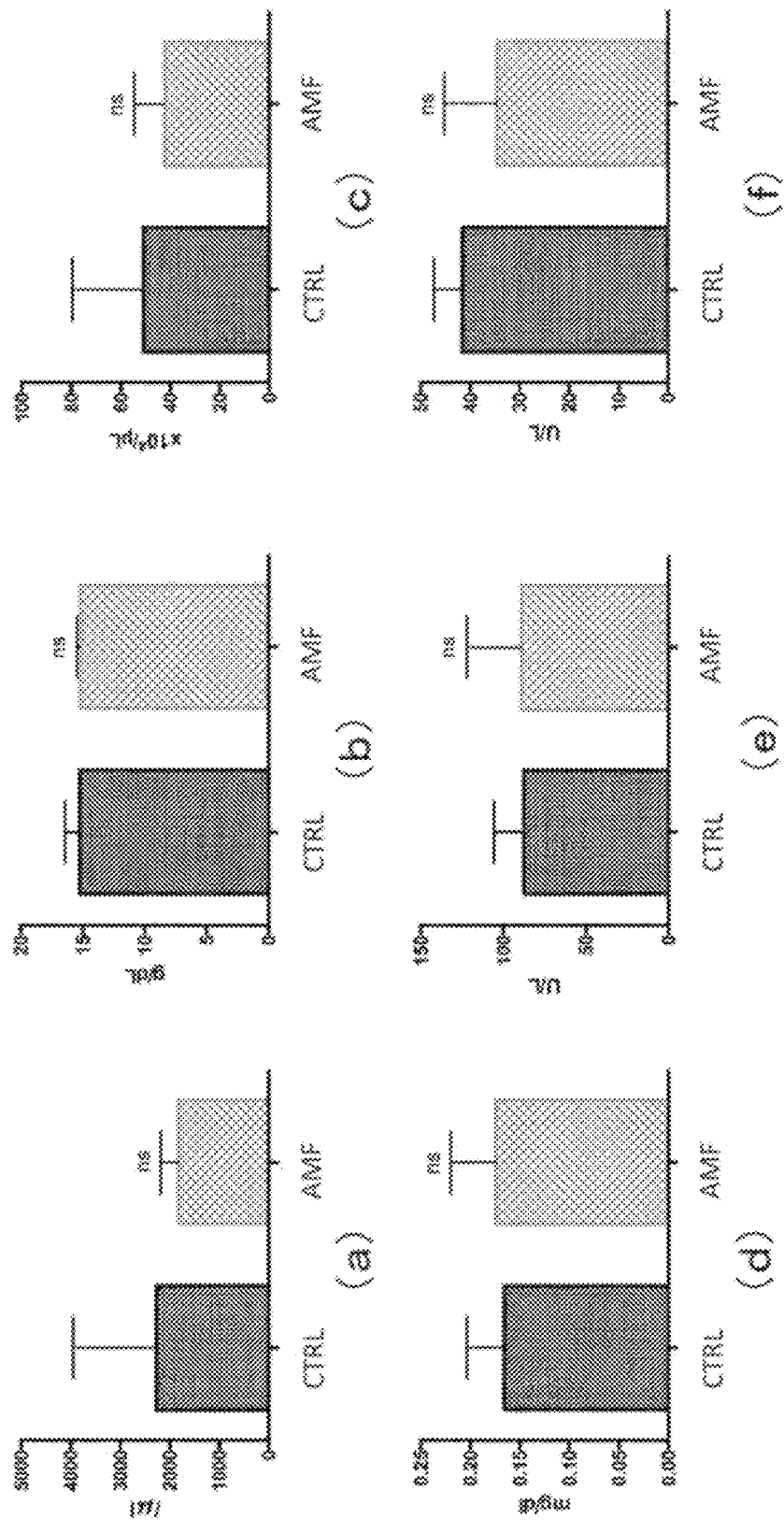
FIG. 26 shows observation results of the side effects according to the example of the present invention.

FIG. 26 is a diagram showing results of the blood test after the elapse of 90 days with respect to the AF group with the tumor transplanted in their cranium and the CTRL group. FIG. 26(*a*) to FIG. 26F sequentially show white blood cells, hemoglobin, blood platelets, AST of the liver functions, and ALT of the liver functions, respectively. Regarding any one of these test results, no significant difference between the CTRL group and the AMF group can be seen, so that no side effect can be acknowledged.

4. Reactive Oxygen

The influence of the application of the alternating magnetic field on reactive oxygen was observed with respect to the human glioblastoma cells (U87), the human glioblastoma cells (U251), the human breast cancer cells (MDAMB231), and the human pancreatic cancer cells (PANC1). Each type of these cells was divided into an AMF group to which the magnetic field was applied, and a CTRL group to which the magnetic field was not applied. Regarding the CTRL group, the alternating magnetic field was applied at 227 kHz for 30 minutes and the reactive oxygen was measured after the elapse of 24 hours.

Figure 29:
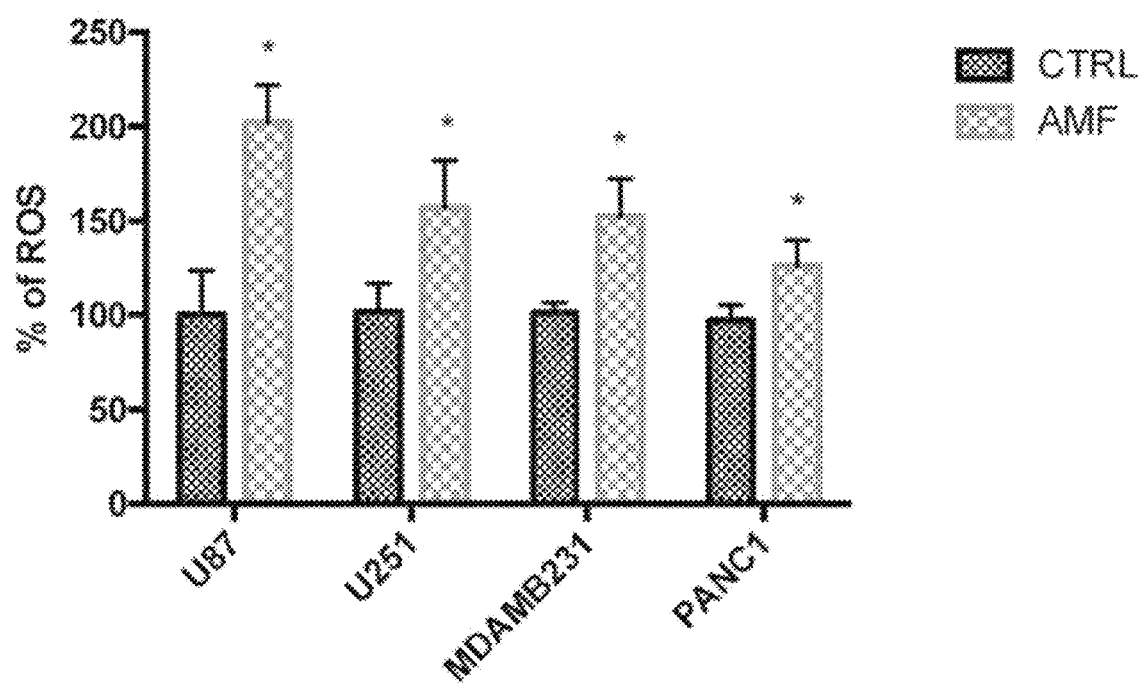
FIG. 29 shows observation results of reactive oxygen according to the example of the present invention.

FIG. 29 is a diagram illustrating the influence of the application of the alternating magnetic field on the reactive oxygen with respect to the human glioblastoma cells (U87), the human glioblastoma cells (U251), the human breast cancer cells (MDAMB231), and the human pancreatic cancer cells (PANC1). Regarding each one of these types of cells, a measured value of the AMF group is indicated by setting a measured value of the CTRL group as 100%. FIG. 29 shows that regarding each one of the human glioblastoma cells (U87), the human glioblastoma cells (U251), the human breast cancer cells (MDAMB231), and the human pancreatic cancer cells (PANC1), the reactive oxygen increased significantly by applying the alternating magnetic field. For example, regarding the human glioblastoma cells (U87), the reactive oxygen of the AMF group increased twice as much as that of the CTRL group.

The present invention exhibits the cancer cell cytostatic effect and the tumor proliferation suppressing effect even on different species from the species explained in the aforementioned examples, for example, on humans. Specifically speaking, the present invention includes a method for treating human cancer cells by using the aforementioned cancer treatment apparatus 100. In other words, the present invention includes a human treatment method which is a method for treating humans by using the cancer treatment apparatus 100.

According to the present invention, the preferred alternating magnetic field for suppressing the tumor proliferation of various cancer types can be applied to the affected tissues for preferred application duration by intuitive and simple operation of devices such as a keyboard and a mouse, and a touch panel. The application duration is short, and the power consumption is small. In addition, the present invention is lightweight. Accordingly, the present invention is a low-cost, highly convenient cancer treatment apparatus. Furthermore, since the affected tissues does not contact the magnetic field generator, the cancer treatment apparatus according to the present invention can be hygienically shared between a plurality of diseased persons.

INDUSTRIAL APPLICABILITY

The present invention is particularly suited for the remission treatment of highly malignant cancers.

The disclosure of the following priority application is herein incorporated by reference. Japanese Patent Application No. 2016-228164 (filed on Nov. 24, 2016)

REFERENCE SIGNS LIST

100: cancer treatment apparatus
200: magnetic field generator

300: power source
400: control module
401: cancer type input unit
402: power switch
403: first input unit
404: second input unit
501: controller
502: memory
503: first output unit
504: timer
505: second output unit
600: coil
601: inner diameter face (0-mm surface) of coil

The invention claimed is:

1. A cancer treatment apparatus for treating a cancer comprising:
   a magnetic field generator that generates a magnetic field of which a frequency is ranged from 100 kHz to 300 kHz to be applied to affected tissues;
   a power source that generates an alternating current to be supplied to the magnetic field generator, and
   a control module that controls the alternating current supplied from the power source to the magnetic field generator, wherein
   the control module controls the alternating current such that a magnetic flux density of the magnetic field, which is generated by the magnetic field generator, is a predetermined value,
   a frequency of the alternating current supplied to the magnetic field generator varies in correspondence with output from the control module,
   wherein the control module controls the power source to maintain a temperature of the affected tissues lower than a cancer cell killing temperature, and
   the control module further includes:
      a cancer type input unit that accepts input depending on a cancer type of the affected tissues wherein the cancer type is defined as an input cancer type;
      a storage unit that stores a plurality of frequencies and cancer types wherein each of the cancer types is associated with at least one of the frequencies; and
      a controller that receives the input cancer type from the cancer type input unit, refers to the storage unit using the input cancer type, and sets a predetermined frequency that is associated with the input cancer type, to the power source such that the magnetic field generator generates the magnetic field with the predetermined frequency and the magnetic flux density of the magnetic field.

2. The cancer treatment apparatus according to claim 1, wherein the storage unit further stores application durations corresponding to the cancer types; and
   wherein the controller refers to the storage unit, determines one of the application durations in correspondence with the input cancer type, and outputs the one of the application durations to the power source.

3. The cancer treatment apparatus according to claim 1, further comprising:
   a power switch that starts supplying the alternating current from the power source to the magnetic field generator.

4. The cancer treatment apparatus according to claim 1, wherein the cancer type input unit can select and input one of the cancer types from a group consisting of a glioblastoma, a malignant melanoma, a tongue cancer, a breast cancer, a malignant mesothelioma, a pancreatic cancer, and a human alveolar basal epithelial adenocarcinoma.

5. The cancer treatment apparatus according to claim 1, wherein the affected tissues are human affected tissues.

6. The cancer treatment apparatus according to claim 2, wherein the application durations stored in the storage unit are ranged from 30 minutes to 180 minutes, inclusive.

* * * * *